US012649934B2

(12) United States Patent (10) Patent No.: US 12,649,934 B2
Sandig et al. (45) Date of Patent: Jun. 9, 2026

(54) HYPERACTIVE TRANSPOSONS AND TRANSPOSASES

(71) Applicant: Probiogen AG, Berlin (DE)

(72) Inventors: Volker Sandig, Berlin (DE); Sven Krügener, Berlin (DE); Thomas Rose, Berlin (DE)

(73) Assignee: PROBIOGEN AG, Berlin (DE)

( * ) Notice: Subject to any disclaimer, the term of this patent is extended or adjusted under 35 U.S.C. 154(b) by 614 days.

(21) Appl. No.: 18/003,282

(22) PCT Filed: Jul. 17, 2020

(86) PCT No.: PCT/EP2020/070320
§ 371 (c)(1),
(2) Date: Dec. 23, 2022

(87) PCT Pub. No.: WO2022/012758
PCT Pub. Date: Jan. 20, 2022

(65) Prior Publication Data
US 2023/0257778 A1 Aug. 17, 2023

(51) Int. Cl.
*C12N 15/90* (2006.01)
*C12N 5/00* (2006.01)
*C12N 9/12* (2006.01)
*C12N 15/85* (2006.01)

(52) U.S. Cl.
CPC ............. *C12N 15/907* (2013.01); *C12N 5/00* (2013.01); *C12N 9/1241* (2013.01); *C12N 15/85* (2013.01); *C12N 2800/90* (2013.01)

(58) Field of Classification Search
CPC ...... C12N 15/907; C12N 5/00; C12N 9/1241; C12N 15/85; C12N 2800/90
See application file for complete search history.

(56) References Cited

U.S. PATENT DOCUMENTS

2006/0212949 A1 9/2006 Alphey

FOREIGN PATENT DOCUMENTS

| JP | 2018-513678 A | 5/2018 |
| WO | 2010/099296 A1 | 9/2010 |
| WO | 2012/074758 A1 | 6/2012 |
| WO | 2015/157579 A2 | 10/2015 |
| WO | 2016/146757 A1 | 9/2016 |
| WO | 2019/126589 A1 | 6/2019 |
| WO | 2019/173636 A1 | 9/2019 |
| WO | 2020/164702 A1 | 8/2020 |

OTHER PUBLICATIONS

International Search Report in PCT/EP2020/070320, mailed May 19, 2021, 7 pages.
Chen et al. Structural basis of seamless excision and specific targeting by piggyBac transposase. Nature communications. Jul. 10, 2020;11(1):1-4.
Solodushko et al. Minimal piggyBac vectors for chromatin integration. Gene therapy. Jan. 2014;21(1):1-9.
Notice of Reasons for refusal in JP2023-503189, mailed Aug. 28, 2024, 5 pages.
Yusa, et al. "A hyperactive piggyBac transposase for mammalian applications." Proceedings of the National Academy of Sciences 108, No. 4 (2011): 1531-1536.

*Primary Examiner* — Tracy Vivlemore
*Assistant Examiner* — Eric J Rogers
(74) *Attorney, Agent, or Firm* — Kilpatrick Townsend & Stockton LLP

(57) ABSTRACT

The present invention relates to a polypeptide comprising a piggyBac transposase or a fragment or a derivative thereof having transposase function comprising at least one amino acid substitution. Further, the present invention relates to a transposable element comprising a piggyBac or piggyBac-like left repeat sequence and left internal repeat sequence, wherein the left internal repeat sequence comprises at least one nucleotide modification. Furthermore, the present invention relates to a kit comprising the above transposase and/or transposable element. In addition, the present invention relates to a targeting system comprising the above transposase and/or transposable element.

11 Claims, 7 Drawing Sheets
Specification includes a Sequence Listing.

FIGURE 2b

PB minimal wild type TES Transposable Element

PB wild type TES Transposable Element (5´TES 248 bp)

PB artificial TES Transposable Element (5´TES 248 bp)

PB wild type TES Transposable Element

PB artificial TES Transposable Element

GOI (SEQ ID NO: 11)

(SEQ ID NO: 12)

(SEQ ID NO: 1)

(SEQ ID NO: 28)

(SEQ ID NO: 13)

(SEQ ID NO: 16)

(SEQ ID NO: 14)

wild type minimal 5´ TES wild type minimal 3´ TES wild type left intern ITR artificial left intern ITR wild type 5´ TES artificial 5´ TES wild type 3´ TES

FIGURE 6

| No. | I30A | Q118P | M185V | M282L | N538R |
|-----|------|-------|-------|-------|-------|
|  |  |  |  |  |  |
| 1 |  |  |  |  | N538R |
| 2 |  |  |  | M282L |  |
| 3 |  |  |  | M282L | N538R |
| 4 |  |  | M185V |  |  |
| 5 |  |  | M185V |  | N538R |
| 6 |  |  | M185V | M282L |  |
| 7 |  |  | M185V | M282L | N538R |
| 8 |  | Q118P |  |  |  |
| 9 |  | Q118P |  |  | N538R |
| 10 |  | Q118P |  | M282L |  |
| 11 |  | Q118P |  | M282L | N538R |
| 12 |  | Q118P | M185V |  |  |
| 13 |  | Q118P | M185V |  | N538R |
| 14 |  | Q118P | M185V | M282L |  |
| 15 |  | Q118P | M185V | M282L | N538R |
| 16 | I30A |  |  |  |  |
| 17 | I30A |  |  |  | N538R |
| 18 | I30A |  |  | M282L |  |
| 19 | I30A |  |  | M282L | N538R |
| 20 | I30A |  | M185V |  |  |
| 21 | I30A |  | M185V |  | N538R |
| 22 | I30A |  | M185V | M282L |  |
| 23 | I30A |  | M185V | M282L | N538R |
| 24 | I30A | Q118P |  |  |  |
| 25 | I30A | Q118P |  |  | N538R |
| 26 | I30A | Q118P |  | M282L |  |
| 27 | I30A | Q118P |  | M282L | N538R |
| 28 | I30A | Q118P | M185V |  |  |
| 29 | I30A | Q118P | M185V |  | N538R |
| 30 | I30A | Q118P | M185V | M282L |  |
| 31 | I30A | Q118P | M185V | M282L | N538R |

HYPERACTIVE TRANSPOSONS AND TRANSPOSASES

CROSS-REFERENCES TO RELATED APPLICATIONS

This application is a U.S. National Stage Application of PCT/EP2020/070320, international filing date 17 Jul. 2020, the disclosure of which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Dec. 19, 2022, is named 1360074-Sequence-Listing.txt and is 49,152 bytes in size.

The present invention relates to a polypeptide comprising a piggyBac transposase or a fragment or a derivative thereof having transposase function comprising at least one amino acid substitution. Further, the present invention relates to a transposable element comprising a piggyBac or piggyBac-like left repeat sequence and left internal repeat sequence, wherein the left internal repeat sequence comprises at least one nucleotide modification. Furthermore, the present invention relates to a kit comprising the above transposase and/or transposable element. In addition, the present invention relates to a targeting system comprising the above transposase and/or transposable element.

BACKGROUND OF THE INVENTION

Transposons have recently been developed as potent, non-viral gene delivery tools. In particular, the performance of a generated producer cell line can be improved, when the integration of plasmid DNA is supported using a transposon. For instance, a transposon allows the integration of a greater size of heterologous DNA and the integration of a higher number of heterologous DNA copies into each genome. Furthermore, integration via a transposon provides an efficient method for the reduction of plasmid backbone integration and/or the reduction of concatemers.

Transposable elements or transposons are DNA-sections, which can move from one locus to another part of the genome. Two classes of transposable elements are distinguished: retrotransposons, which replicate through an RNA intermediate (class 1), and "cut-and-paste" DNA transposons (class 2). Class 2 transposons are characterised by short inverted terminal repeats (ITRs) and element-encoded transposases, enzymes with excision and insertion activity. In the natural configuration, the transposase gene is located between the inverted repeats. A number of class 2 transposons have been shown to facilitate insertion of heterologous DNA into the genome of eukaryotes, for example, a transposon from the moth *Trichoplusia ni* (piggyBac), a transposon from the bat *Myotis lucifugus* (piggyBat), a reconstructed transposon from salmon species (Sleeping Beauty), or a transposon from the medaka *Oryzias latipes* (Tol2). These transposons have many applications in genetic manipulation of a host genome, including transgene delivery and insertional mutagenesis. For instance, the piggyBac (PB) DNA transposon (previously described as IFP2) is used technologically and commercially in genetic engineering by virtue of its property to efficiently transpose between vectors and chromosomes [U.S. Pat. No. 6,218,185 B1]. For these applications the DNA to be integrated is flanked by two PB ITRs in a PB vector. By co-delivery of PB transposase the flanked DNA is excised precisely form the PB vector and integrated into the target genome at TTAA specific sites.

To increase transformation efficiencies, more active transposases were developed. These hyperactive transposases yield a greater fraction of cells that integrated a provided transposon and a greater number of transposon integrations per cell compared to wild-type transposases. Different strategies are described in the art: For example, EP2160461 B1 describes hyperactive Sleeping Beauty transposases generated via side directed mutagenesis, U.S. Pat. No. 9,534,234 B2 provides a PB-like transposase derived from the silkworm *Bombyx mori* and from the frog *Xenopus tropicalis* fused to a heterologous nuclear localization sequence (NLS), EP1546322 B1 discloses a chimeric integrating enzyme comprising a binding domain recognising a DNA landing pad to drag transposon-transposase complex to the landing pad and promote integration in its vicinity and EP1594972 B1 claims a transposase or a fragment or derivative thereof having transposase function fused to a polypeptide binding domain that can associates with a cellular or engineered polypeptide comprising a DNA targeting domain.

Transformation efficiencies can also be increased by using more active transposons.

One field of application for transposases is the development of pharmaceutical cell lines. Chinese Hamster Ovary (CHO) cells are the most prevalent mammalian cell factories for producing therapeutic biologics, due to its ability to grow in suspension cultures, its capacity for complex post-translational modifications, and its low susceptibility to human viral infections. One of the main limits for the industrial production of recombinant therapeutic proteins is the time- and labor-intensive process of cell line production and characterisation. The majority of the available methods rely on random transgene integration. Multiple cassettes often integrate in tandem into more or less active sites. Active chromosomal loci are rare and thousands of clones have to be screened to obtain high producers. To reduce the extent of recombinant cell line screening and to enhance the productivity and stability of recombinant CHO cell lines, PB-mediated gene delivery was used [M. Matasci et al., The PiggyBac transposon enhances the frequency of CHO stable cell line generation and yields recombinant lines with superior productivity and stability. Biotechnology and Bioengineering, Vol. 108, No. 9, (2011)].

The results with respect to more active transposons and transposases (e.g. more active PB and PB-like transposons and transposases) are, however, not (yet) satisfying.

It would be highly desirable to develop transposons and transposases (e.g. PB and PB-like transposons and transposases) yielding a greater number of transposon integrations per cell compared to the state of the art.

Recently, Morellet et al., reported, that the C-terminal Cysteine-Rich Domain (CRD) of the PB transposase binds to specific DNA sequences in the left and right transposon ends, and to an additional unexpectedly internal site at the left end (Nucleic Acids Research, 2018, Vol. 46, No. 5 2018 doi: 10.1093/nar/gky044).

The present inventors surprisingly found that artificially inserted modifications within the left internal repeat sequence of transposable elements reduce the viability recovery time during selection phase of transfectants. Artificial piggyBac (PB) and PB-like transposable elements with at least one modification within the left internal repeat sequence, which increases the homology of the left internal repeat sequence to the left repeat sequence, are not described or suggested in art. It was unlikely that such mutations would have any effect at all.

In addition, the present inventors surprisingly established for the first time a targeting system/genetic delivery system comprising a transposable element comprising a piggyBac (PB) or PB-like artificial left internal repeat sequence for the improved generation of producer cell lines for the production of therapeutic proteins or for the production of biopharmaceutical products based on virus particles in high yields. Moreover, the present inventors surprisingly found hyperactive piggyBac (PB) transposases capable to mobilize a transposon, e.g. the transposable element described here, from one genomic location to another with a higher effectivity than piggyBac (PB) transposases described in art.

SUMMARY OF THE INVENTION

In a first aspect, the present invention relates to a polypeptide comprising a piggyBac transposase or a fragment or a derivative thereof having transposase function comprising at least one amino acid substitution selected from the group consisting of isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

In a second aspect, the present invention relates to a polynucleotide encoding the polypeptide according to the first aspect.

In a third aspect, the present invention relates to a vector comprising the polynucleotide according to the second aspect.

In a fourth aspect, the present invention relates to a transposable element comprising a piggyBac or piggyBac-like left repeat sequence and left internal repeat sequence, wherein the left internal repeat sequence comprises at least one nucleotide modification, wherein the at least one nucleotide modification increases the homology of the left internal repeat sequence to the left repeat sequence.

In a fifth aspect, the present invention relates to a method for producing a transgenic cell comprising the steps of:

(i) providing a cell, and (ii) introducing (iia) a transposable element, and a polypeptide according to the first aspect, or a polynucleotide according to the second aspect, or a vector according to the third aspect, or (iib) a transposable element according to the fourth aspect, and a transposase or a fragment or a derivative thereof having transposase function, or a polynucleotide encoding a transposase or a fragment or a derivative thereof having transposase function, or a vector comprising a polynucleotide encoding a transposase or a fragment or a derivative thereof having transposase function, or (iic) a transposable element according to the fourth aspect, and a polypeptide according to the first aspect, or a polynucleotide according to the second aspect, or a vector according to the third aspect into the cell, thereby producing the transgenic cell.

In a sixth aspect, the present invention relates to a transgenic cell obtainable by the method according to the fifth aspect.

In a seventh aspect, the present invention relates to the use of a transgenic cell according to the sixth aspect for the production of a protein or virus.

In an eight aspect, the present invention relates to a kit comprising (i) a transposable element, and a polypeptide according to the first aspect, or a polynucleotide according to the second aspect, or a vector according to the third aspect; or (ii) a transposable element according to the fourth aspect, and a transposase or a fragment or a derivative thereof having transposase function, or a polynucleotide encoding a transposase or a fragment or a derivative thereof having transposase function, or a vector comprising a polynucleotide encoding a transposase or a fragment or a derivative thereof having transposase function; or (iii) a transposable element according to the fourth aspect, and a polypeptide according to the first aspect, or a polynucleotide according to the second aspect, or a vector according to the third aspect.

In a ninth aspect, the present invention relates to a targeting system comprising (i) a transposable element, and a polypeptide according to the first aspect, or a polynucleotide according to the second aspect, or a vector of according to the third aspect; or (ii) a transposable element according to the fourth aspect, and a transposase or a fragment or a derivative thereof having transposase function, or a polynucleotide encoding a transposase or a fragment or a derivative thereof having transposase function, or a vector comprising a polynucleotide encoding a transposase or a fragment or a derivative thereof having transposase function; or (iii) a transposable element according to the fourth aspect, and a polypeptide according to the first aspect, or a polynucleotide according to the second aspect, or a vector of according to the third aspect.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU-PAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The terms "polypeptide" and "protein" are used interchangeably in the context of the present invention and refer to a long peptide-linked chain of amino acids.

The term "polypeptide fragment" as used in the context of the present invention refers to a polypeptide that has a deletion, e.g. an amino-terminal deletion, and/or a carboxy-terminal deletion, and/or an internally deletion compared to the full-length polypeptide.

The term "transposase", as used herein, refers to any enzyme that is able to bind to the ends of a transposable element and to catalyze its movement to another part of the genome by a cut and paste mechanism or a replicative transposition mechanism. The ends of a transposable element are preferably terminal repeats, e.g. terminal inverted repeats (TIRs). Thus, a transposase is not only able to recognize the terminal repeats surrounding the mobile element, it is also able to recognize target sequences, e.g. on the new host DNA.

The term "fragment" of a transposase "having transposase function", as used herein, refers to a fragment derived from a naturally occurring transposase which lacks one or more amino acids compared to the naturally occurring transposase and has transposase function. For example, said fragment of a naturally occurring transposase has still transposase function, in particular still mediates nucleotide sequence, e.g. DNA, excision and/or insertion. Generally, a fragment of an amino acid sequence contains less amino acids than the corresponding full length sequence, wherein the amino acid sequence present is in the same consecutive order as in the full length sequence. As such, a fragment does not contain internal insertions or deletions of anything into the portion of the full length sequence represented by the fragment.

The term "derivative" of a transposase "having transposase function", as used herein, refers to a derivative of a naturally occurring transposase, wherein one or more amino acids have been substituted, deleted, inserted, and/or added compared to the naturally occurring transposase and has transposase function. For example, said derivative of a naturally occurring transposase has still transposase function, in particular still mediates nucleotide sequence, e.g. DNA, excision and/or insertion. In contrast to a fragment, a derivative may contain internal insertions or deletions within the amino acids that correspond to the full length sequence, or may have similarity to the full length coding sequence.

The above described modifications are preferably effected by recombinant DNA technology. Further modifications may also be effected by applying chemical alterations to the transposase.

The transposase as well as fragments or derivatives thereof, may be recombinantly produced and yet may retain identical or essentially identical features as the naturally occurring transposase, in particular with respect to nucleotide sequence, e.g. DNA, excision and/or insertion. For example, the transposase fragment or derivative referred to herein preferably maintains at least 50% of the activity of the native protein, more preferably at least 75%, and even more preferably at least 95% of the activity of the native protein. Such biological activity is readily determined by a number of assays known in the art, for example, enzyme activity assays.

The (hyperactive/artificial) transposase or fragment or derivative thereof having transposase function according to the present invention comprises at least one amino acid substitution selected from the group consisting of isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

This transposase or fragment or derivative thereof has an improved transposase function, in particular an improved activity/ability to mediate nucleotide sequence, e.g. DNA, excision and/or insertion, compared to transposases described in art (e.g. wild-type/naturally occurring transposases). In particular, this transposase or fragment or derivative thereof is able to mobilize a transposon, e.g. the transposable element described herein, from one genomic location to another with a higher effectivity than transposases described in art (e.g. wild-type/naturally occurring transposases).

This transposase or fragment or derivative thereof may be recombinantly produced and yet may have improved features compared to the transposases described in the art (e.g. wild-type/naturally occurring transposase), in particular with respect to nucleotide sequence, e.g. DNA, excision and/or insertion. For example, this transposase fragment or derivative referred to herein preferably has an activity which is at least 10% above the activity of the native protein, more preferably at least 20% above the activity of the native protein, even more preferably at least 50% above the activity of the native protein, and most preferably at least 75% above of the activity of the native protein. Such biological activity is readily determined by a number of assays known in the art, for example, enzyme activity assays.

This transposase or fragment or derivative thereof may be designated as a recombinant, an artificial, and/or a heterologous transposase or fragment or derivative thereof.

The transposase or fragment or derivative thereof having transposase function of the present invention can be designated as hyperactive transposase or fragment or derivate thereof. The term "hyperactive transposase or fragment or derivate thereof", as used herein, refers to a transposase or fragment or derivate thereof with improved transposase function, in particular an improved activity/ability to mediate nucleotide sequence, e.g. DNA, excision and/or insertion compared to the transposases described in art (e.g. wild-type transposases). In particular, the "hyperactive transposase or fragment or derivate thereof", as used herein, refers to a transposase or fragment or derivate thereof which is able to mobilize a transposon, e.g. the transposable element described herein, from one genomic location to another with a higher effectivity than transposases described in art (e.g. wild-type transposases).

Histones are building blocks of chromatin. Histone posttranslational modifications form a signature that is indicative of the chromatin state of a given loci. Euchromatin is generally associated with high levels of histone acetylation and/or methylation, in particular mono-methylation. In particular, acetylation, e.g. of lysine residues, can reduce the positive charge of histones, thereby weakening their interaction with negatively charged DNA and increasing nucleosome (complex of DNA and histone) fluidity. Also amino acid acetylation can reduce the compaction level of a nucleosomal array. The chromatin state of a given loci depends, for example, on molecules which can posttranslationally modify, e.g. methylate and/or acetylate, histones (so called "writers"), molecules which can remove posttranslational modifications, e.g. methylated and/or acetylated histones (so called "erasers"), and molecules, which can readily identify posttranslational modifications of histones, e.g. methylations and/or acetylations, (so called "readers"). The "reader" molecules are recruited to such histone modifications and bind via specific domains, e.g. plant homeodomain (PHD) zinc finger, bromodomain, or chromodomain. The triple action of "writing", "reading", and "erasing" establishes the favourable local environment for transcriptional regulation, DNA damage repair, etc.

The term "chromatin reader element (CRE)", as used herein, refers to any structure providing an accessible surface (such as a cavity or surface groove) to accommodate a modified histone residue and determine the type of post-translational histone modification (e.g. acetylation or methylation and acetylation versus methylation) or state specificity (such as mono-methylation, di-methylation, versus tri-methylation, e.g. of lysines or arginines). A "chromatin reader element" also interacts with the flanking sequence of the modified amino acid in order to distinguish sequence context. In particular, a "chromatin reader element" binds histone tails and recognizes specific post-translational modifications (PTMs), e.g. methylations, such as lysine or arginine methylations, and/or acetylations, on the histones. As a consequence, the chromatin reader element recruits chromatin remodelling complexes and components of the transcriptional machinery to the binding position. The "chromatin reader element" is preferably an element recognizing the histone methylation degree, in particular histone mono-methylation, di-methylation or, tri-methylation degree, e.g. of lysine and/or arginine residues. Alternatively, the "chromatin reader element" is an element recognizing the acetylation state of histones. As mentioned above, transcriptionally active euchromatin is generally associated with histone acetylation and/or methylation, in particular histone mono-methylation. It is preferred that the the chromatin reader element is a "chromatin reader domain (CRD)". The chromatin reader domain may be a bromodomain, a chromodomain, a plant homeodomain (PHD) zinc finger, a WD40 domain, a tudor domain, double/tandem tudor domain, a MBT domain, an ankyrin repeat domain, a zf-CW domain, or a PWWP domain. For example, bromodomains are found in chromatin-associated proteins like histone acetyltransferases specifically recognizing acetylated lysine residues. PHDs (in particular PHD fingers) are also found in chromatin-associated proteins like plant homeodomain proteins such as transcription initiation factors. They can also recognize acetylated lysine residues. Chromatin reader domains that recognize histone methylation include PHD domains, chromodomains, WD40 domains, tudor domains, double/tandem tudor domains, MBT domains, ankyrin repeat domains, zf-CW domains, and PWWP domains. It is more preferred that the chromatin reader domain is a bromodomain or a plant homeodomain (PHD) zinc finger. It is alternatively preferred that the chromatin reader element is an artificial chromatin reader element. The artificial chromatin reader element may be a micro antibody, a single chain antibody, an antibody fragment, an affibody, an affilin, an anticalin, an atrimer, a DARPin, a FN2 scaffold, a fynomer, or a Kunitz domain.

The chromatin reader element, in particular chromatin reader domain, may be associated with a transposase, or a fragment, or a derivative thereof having transposase function. The transposase, or a fragment, or a derivative thereof having transposase function connected to a chromatin reader element, in particular chromatin reader domain, is able to recognize specific histone post-translational modifications, such as methylations and/or acetylations and, thus, active euchromatin.

The term "DNA binding/targeting domain", as used herein, refers to a moiety that is capable of specifically binding to a DNA region (including chromosomal regions of higher order structure such as repetitive regions in the nucleus) and is, directly or indirectly, involved in mediating integration of a transposable element into said DNA region. The DNA region would preferably be defined by a nucleotide sequence which is unique within the respective genome.

The term "nuclear localization sequence/signal (NLS)", as used herein, refers to a structure that tags a polypeptide for import into the cell nucleus by nuclear transport. Typically, this sequence/signal consists of one or more short sequences of positively charged lysines or arginines exposed on the surface of the polypeptide.

The term "heterologous", as used herein, refers to an element that is either derived from another natural source, e.g. another organism, or is taken out of its natural context, e.g. fused, attached, or coupled to another molecule, or is not normally found in nature. In particular, the term "heterologous polypeptide", as used in the context of the present invention, refers to a polypeptide that is not normally found in nature. The term "heterologous nucleotide sequence", as used in the context of the present invention, refers to a nucleotide sequence that is not normally found in nature. The term encompasses a nucleic acid wherein at least one of the following is true: (a) the nucleic acid that is exogenously introduced into a given cell (hence "exogenous sequence" even though the sequence can be foreign or native to the recipient cell), (b) the nucleic acid comprises a nucleotide sequence that is naturally found in a given cell (e.g. the nucleic acid comprises a nucleotide sequence that is endogenous to the cell) but the nucleic acid is either produced in an unnatural (e.g. greater than expected or greater than naturally found) amount in the cell, or the nucleotide sequence differs from the endogenous nucleotide sequence such that the same encoded protein (having the same or substantially the same amino acid sequence) as found endogenously is produced in an unnatural (e.g. greater than expected or greater than naturally found) amount in the cell, or (c) the nucleic acid comprises two or more nucleotide sequences or segments that are not found in the same relationship to each other in nature (e.g., the nucleic acid is recombinant).

The terms "heterologous chromatin reader element (CRE), in particular chromatin reader domain (CRD)", "heterologous DNA binding domain" or "heterologous nuclear localization sequence (NLS)" as used herein in connection with a transposase or a fragment or a derivative thereof having transposase function, refer to amino acid sequences that are normally not found intimately associated with a transposase, or a fragment or a derivative thereof having transposase function in nature.

The term "transposable element (also designated as "transposon" or "jumping gene")", as used herein, refers to a polynucleotide molecule that can change its position within the genome. Usually, the transposable element includes a polynucleotide encoding a functional transposase that catalyses excision and insertion. However, the transposable element described in the context of the present invention is devoid of a polynucleotide encoding a functional transposase. The transposon based polynucleotide molecule described herein no longer comprises the complete sequence encoding a functional, preferably a naturally occurring, transposase. Preferably, the complete sequence encoding a functional, preferably a naturally occurring, transposase or a portion thereof, is deleted from the transposable element. Alternatively, the gene encoding the transposase is mutated such that a naturally occurring transposase or a fragment or derivative thereof having the function of a transposase, i.e. mediating the excision and/or insertion of a transposon into a target site, is no longer contained. The transposable element described herein retains sequences that are required for mobilization by the transposase provided in trans. These are the repetitive sequences at each end of the transposable element containing the binding sites for the transposase allowing the excision and integration. Said repetitive sequences are also called terminal repeats. Preferably, the terminal repeats are terminal inverted repeats (TIRs). In particular, the terminal repeats are piggyBac terminal repeats or piggyBac-like terminal repeats. The end sequences of a transposable element are also designated as "5'-transposon end sequence" and "3'-transposon end sequence" herein.

Instead of polynucleotide sequences encoding a functional transposase, exogenous polynucleotide sequences, e.g. polynucleotide sequences of interest/heterologous polynucleotide sequences such as functional genes and regulatory elements driving expression, are preferably part of the transposable element described herein. In particular, theses sequences are located between the terminal repeats. In other words, these sequences are located between the "5'-transposon end sequence" and the "3'-transposon end sequence".

Preferably, the transposase recognises a TA dinucleotide at each end of the transposable element, particularly at the repetitive sequences of the transposable element and excises the transposable element, e.g. from a vector. Usually, two transposase monomers are involved in the excision of the transposable element, one transposase monomer at each end of the transposable element. Finally, the transposase dimer in complex with the excised transposable element reintegrates the transposable element in the DNA of a host organism, e.g. host cell, by recognising a TTAA site in the target sequence.

The terms "5'-transposon end sequence" and "3'-transposon end sequence", as used herein, refer to the parts of the 5' and 3' non-coding region of the transposable element described herein, which are responsible for identifying the transposable element by a transposase. They are capable of forming a functional complex with the transposase to perform a transposition reaction. Other functional elements like enhancers and/or promoters may be embedded within transposon end sequences. For the piggyBac transposable element, the most commonly used vector configuration today is a 5'-transposon end sequence with a length of 311 bp and a 3'-transposon end sequence with a length of 235 bp.

The 5'-transposon end sequence of the transposable element described herein comprises a left repeat sequence and a left internal repeat sequence.

The term "left repeat sequence", as used herein, refers to a nucleotide sequence located between the 5' end and the left internal repeat sequence of the transposon. In particular, the left repeat sequence is located within the first 80 nucleotides of the 5'-transposon end sequence and binds to the PB Cysteine-Rich Domain or the PB-like Cysteine-Rich Domain. For example, the left repeat sequence of the original PB is a 19 bp DNA-region separated by a 3 bp spacer from the 13 bp terminal inverted repeat. It is highly homolog to the right repeat sequence and (highly) homolog to the left internal repeat sequence.

The term "left internal repeat sequence", as used herein, refers to a nucleotide sequence located downstream of the left repeat sequence within the 5'-transposon end sequence of the transposon. It is (highly) homolog to the left repeat sequence. It is, for example, protected in DNA-footprint assays by cross-brace zinc finger motif of piggyBac or piggyBac-like transposase. Recently, Morellet et al., reported, that the C-terminal Cysteine-Rich Domain (CRD) of the PB transposase binds to specific DNA sequences in the left and right transposon ends, and to an additional unexpectedly internal site at the left end (Nucleic Acids Research, 2018, Vol. 46, No. 5 2018 doi: 10.1093/nar/gky044).

The left repeat sequence and the left internal repeat sequence comprised in/part of the 5'-transposon end sequence may be connected with each other by natural transposable element sequences or by non-naturally transposable element sequences, e.g. by (heterologous) linker sequences.

The term "piggyBac (PB) transposon", as used herein, refers to a transposon derived from cabbage looper moth *Trichoplusia ni*. The transposable segments were initially discovered in mutant baculovirus strains, hence their name "PB". The original PB element is approximately 2.4 kb with identical 13 bp terminal inverted repeats and additional asymmetric 19 bp internal repeats. These asymmetric 19 bp internal repeats are also designated as "left repeat sequence" and "right repeat sequence". The term "piggyBac (PB) transposase", as used herein, refers to a transposase derived from cabbage looper moth *Trichoplusia ni* (GenBank accession number #AAA87375.2; SEQ ID NO: 18 [Virology 172(1) 156-169 1989]).

The term "piggyBac- (PB-) like transposon", as used herein, refers to another transposon than the transposon derived from cabbage looper moth *Trichoplusia ni* but having the same genetic structure. PiggyBac- (PB-) like transposons include left repeat sequences of approximately 12-17 bases and are flanked by a 4 base sequence corresponding to the integration target sequence which is duplicated on transposon integration. For example, a piggyBac- (PB-) like transposon may be derived from *Xenopus tropicalis, Bombyx mori* (silk worm), *Mus musculus, Homo sapiens* or *Myotis lucifugus*. The term "piggyBac- (PB-) like transposase", as used herein, refers to another transposase than the transposase derived from cabbage looper moth *Trichoplusia ni*. It is characterized by a DDE-like DDD motif with aspartate residues at positions corresponding to D268, D346, and D447 of *Trichoplusia ni* PB transposase (SEQ ID NO: 18). PiggyBac- (PB-) like transposons and transposases occur naturally in a wide range of organisms (Sakar, A. et. al., (2003). Mol. Gen. Genomics 270: 173-180). For example, a piggyBac- (PB-) like transposase may be derived from *Xenopus tropicalis, Bombyx mori* (silk worm), *Mus musculus, Homo sapiens* or *Myotis lucifugus*.

The (hyperactive/artificial) transposable element of the present invention comprises a piggyBac or piggyBac-like
    left repeat sequence and
    left internal repeat sequence,
    wherein the left internal repeat sequence comprises at
        least one nucleotide modification,
    wherein the at least one nucleotide modification increases
        the homology of the left internal repeat sequence to the
        left repeat sequence.
    The at least one nucleotide modification is preferably
        selected from the group consisting of a nucleotide
        substitution, a nucleotide deletion, a nucleotide addition, and a nucleotide insertion, or is a combination
        thereof.
    This transposable element reduces the viability recovery
        time during selection phase of transfectants compared
        to the transposable element of the state of the art (e.g.
        wild-type transposable element).
    This transposable element may be designated as a recombinant, an artificial, and/or a heterologous transposable
        element.
The term "polynucleotide", as used herein, means a polymer of deoxyribonucleotide bases or ribonucleotide bases and includes DNA and RNA molecules, both sense and anti-sense strands. In detail, the polynucleotide may be DNA, both cDNA and genomic DNA, RNA, mRNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine. Polynucleotides may be obtained by chemical synthesis methods or by recombinant methods. Preferably, the polynucleotide is a DNA or mRNA molecule.

The term "polynucleotide of interest", as used herein, relates to a nucleotide sequence. The nucleotide sequence may be a RNA or DNA sequence, preferably the nucleotide sequence is a DNA sequence. In accordance with the different aspects of the present invention, the polynucleotide of interest may encode for a product of interest. A product of interest may be a polypeptide of interest, e.g. a protein, or a RNA of interest, e.g. a mRNA or a functional RNA, e.g. a double stranded RNA, microRNA, or siRNA. Functional RNAs are frequently used to silence a corresponding target gene. Preferably, the polynucleotide of interest is operatively liked to suitable regulatory sequences (e.g. a promoter) which are well known and well described in the art and which may affect the transcription of the polynucleotide of interest.

The level of expression of a desired product in a host organism, e.g. host cell, may be determined on the basis of either the amount of corresponding mRNA that is present in the cell, or the amount of the desired product encoded by polynucleotide of interest. For example, mRNA transcribed from a selected sequence can be quantitated by PCR or by Northern hybridization. Polypeptides can be quantified by various methods, e.g. by assaying for the biological activity of the polypeptides (e.g. by enzyme assays), or by employing assays that are independent of such activity, such as western blotting, ELISA, or radioimmunoassay, using antibodies that recognize and bind to the protein.

The polynucleotide of interest is preferably selected from the group consisting of a polynucleotide encoding a polypeptide, a non-coding polynucleotide, a polynucleotide comprising a promoter sequence, a polynucleotide encoding a mRNA, a polynucleotide encoding a tag, and a viral polynucleotide. The polynucleotide of interest is preferably a heterologous/exogenous polynucleotide.

The term "expression control sequences", as used herein, refers to nucleotide sequences which affect the expression of coding sequences to which they are operably linked in a host organism, e.g. host cells. Expression control sequences are sequences which control the transcription, e.g. promoters, TATA-box, enhancers, UCOE or MAR elements, polyadenylation signals, post-transcriptionally active elements, e.g. RNA stabilising elements, RNA transport elements and translation enhancers.

The term "operably linked", as used herein, means that one nucleotide sequence is linked to a second nucleotide sequence in such a way that in-frame expression of a corresponding fusion or hybrid protein can be affected avoiding frame-shifts or stop codons. This term also means the linking of expression control sequences to a coding nucleotide sequence of interest (e.g. coding for a protein) to effectively control the expression of said sequence. This term further means the linking of a nucleotide sequence encoding an affinity tag or marker tag to a coding nucleotide sequence of interest (e.g. coding for a protein).

The term "linker", as used herein, refers to a stretch of amino acids, e.g. of at least 2, 3, 4, or 5 amino acids, or to a stretch of nucleotides, e.g. of at least 2, 3, 4, 5, 6, 7, 8, 9, or 10 nucleotides, which does not fulfil a biological function within a host organism such as a cell. The function of a linker is to tether or combine different polypeptides or polynucleotides allowing these polypeptides or polynucleotides to exert their biological functions that they would exert without being attached to said linker.

The term "minicircles" as used herein, refers to DNA vectors that are produced as circular expression cassettes devoid of any bacterial plasmid DNA backbone.

A "variant" as used herein, can be characterized by a certain degree of sequence identity to the parent amino acid sequence or nucleotide sequence from which it is derived. More precisely, an amino acid sequence variant in the context of the present invention may exhibit at least 80% sequence identity to its parent amino acid sequence. A nucleotide sequence variant in the context of the present invention may exhibit at least 80% sequence identity to its parent nucleotide sequence. The term "at least 80% identical to", as used herein, refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective parent/reference amino acid sequence or to the respective parent/reference nucleotide sequence. Preferably, the amino acid sequence in question and the parent/reference amino acid sequence exhibit the indicated sequence identity over the entire length of the parent/reference amino acid sequence. Preferably, the nucleotide sequence in question and the parent/reference nucleotide sequence exhibit the indicated sequence identity over the entire length of the parent/reference nucleotide sequence.

The "(hyperactive/artificial) transposable element" of the present invention reduces the viability recovery time during selection phase of transfectants compared to the transposable element of the state of the art (e.g. wild-type transposable element).

The "(hyperactive) transposable element variants" of the present invention retain/also have the above-mentioned advantageous effects. In addition, they still serve as substrates for transposases. Thus, these variants are functionally active variants.

The transposable elements or transposable element variants of the present invention can be designated as recombinant, heterologous, artificial, and/or modified transposable elements or transposable element variants.

The "(hyperactive/artificial) transposase or fragment or derivate thereof" of the present invention has improved transposase function, in particular an improved activity/ability to mediate nucleotide sequence, e.g. DNA, excision and/or insertion. The "transposase or fragment or derivate thereof" of the present invention is also able to mobilize a transposon, e.g. the transposable element described herein, from one genomic location to another with a higher effectivity than transposases described in art (e.g. wild-type transposases).

The "(hyperactive) transposase variants" of the present invention retain/also have the above-mentioned advantageous effects. In addition, they still recognize the transposable element as a substrate. Thus, these variants are functionally active variants.

The transposase or transposase variants of the present invention can be designated as recombinant, heterologous, artificial, and/or modified transposase or transposase variants.

The similarity of nucleotide and amino acid sequences, i.e., the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson J. D. et al. Nucleic Acids Res. 1994, 22:4673-80) available e.g. on http://www.ebi.ac.uk/Tools/clustalw/ or on http://www.ebi-.ac.uk/Tools/clustalw2/index.html or on http://npsa-pbil-.ibcp.fr/cgi-bin/npsa_automat.pl?page=/NPSA/npsa_clust-alw.html. Preferred parameters used are the default parameters as they are set on http://www.ebi.ac.uk/Tools/clustalw/ or http://www.ebi.ac.uk/Tools/clustalw2/index-.html. The grade of sequence identity (sequence matching) may be calculated using e.g. BLAST, BLAT or BlastZ (or BlastX). A similar algorithm is incorporated into the BLASTN and BLASTP programs of Altschul et al. J. Mol. Biol. 1990, 215:403-410. To obtain gapped alignments for comparative purposes, Gapped BLAST is utilized as described in Altschul et al. Nucleic Acids Res. 1997, 25:3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

Residues in two or more polypeptides or polynucleotides are said to "correspond" to each other if the residues occupy an analogous position in the polypeptide or nucleotide structures. It is well known in the art that analogous positions in two or more polypeptides can be determined by aligning the polypeptide sequences based on amino acid sequence or structural similarities. It is also well known in the art that analogous positions in two or more polynucleotides can be determined by aligning the polynucleotide sequences based on nucleotide sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

The term "host cell", as used herein, refers to any cell which may be used for protein and/or virus production. It also refers to any cell which may be the host for the polypeptide, polynucleotide and/or transposable element described herein. The cell may be a prokaryotic or an eukaryotic cell. Preferably, the cell is an eukaryotic cell. More preferably, the eukaryotic cell is a vertebrate, a yeast, a fungus, or an insect cell. The vertebrate cell may be a mammalian, a fish, an amphibian, a reptilian cell or an avian cell. The avian cell may be a chicken, a quail, a goose, or a duck cell such as a duck retina cell or duck somite cell. Even more preferably, the vertebrate cell is a mammalian cell. Most preferably, the mammalian cell is selected from the group consisting of a Chinese hamster ovary (CHO) cell (e.g. CHO-K1/CHO-S/CHO-DUXB11/CHO-DG44 cell), a human embryonic kidney (HEK293) cell, a HeLa cell, a A549 cell, a MRCS cell, a WI38 cell, a AGE1.CR cell, a BHK cell, and a Vero cell. The cell may also be comprised in/part of an organism. Said organism may be a prokaryotic or an eukaryotic organism. Preferably, the organism is an eukaryotic organism. More preferably, said organism may be a fungus, an insect, or a vertebrate. The vertebrate may be a bird (e.g. a chicken, quail, goose, or duck), a canine, a mustela, a rodent (e.g. a mouse, rat or hamster), an ovine, a caprine, a pig, a bat (e.g. a megabat or microbat) or a human/non-human primate (e.g. a monkey or a great ape).

Most preferably the organism is a mammal such as a mouse, a rat, a pig, or a human/non-human primate.

EMBODIMENTS OF THE INVENTION

The present inventors surprisingly found hyperactive piggyBac (PB) transposases capable to mobilize a transposon, e.g. the transposable element described here, from one genomic location to another with a higher effectivity than piggyBac (PB) transposases described in art (e.g. wild-type transposases). In addition, the present inventors surprisingly found that artificially inserted modifications within the left internal repeat sequence of transposable elements reduce the viability recovery time during selection phase of transfectants. Artificial piggyBac (PB) and PB-like transposable elements with at least one modification within the left internal repeat sequence, which increases the homology of the left internal repeat sequence to the left repeat sequence, are not described or suggested in art. It was unlikely that such modifications would have any effect at all.

Moreover, the present inventors surprisingly established for the first time a targeting system/genetic delivery system comprising a transposable element comprising a piggyBac (PB) or PB-like artificial left internal repeat sequence for the improved generation of producer cell lines for the production of therapeutic proteins or for the production of biopharmaceutical products based on virus particles in high yields.

Thus, in a first aspect, the present invention relates to a(n) (recombinant/artificial) polypeptide comprising, consisting essentially of, or consisting of a (hyperactive) piggyBac transposase or a fragment or a derivative thereof having transposase function comprising at least one amino acid substitution (e.g. at least 1, 2, 3, 4, or 5 amino acid substitution(s)) selected from the group consisting of isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

Single substitutions and combinations of substitutions of the piggyBac transposase or fragment or derivative thereof are listed in FIG. 6.

In one preferred embodiment, the piggyBac transposase or the fragment or the derivative thereof having transposase function comprises the following amino acid substitutions:

isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

In one more preferred embodiment, the piggyBac transposase or the fragment or the derivative thereof having transposase function comprises the following amino acid substitutions:

isoleucine (I) at amino acid position 30 or at an amino acid position corresponding thereto is replaced by alanine (A) (I30A), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

The wild-type piggyBac transposase has preferably a nucleotide sequence according to SEQ ID NO: 17 and an amino acid sequence according to SEQ ID NO: 18. Thus, in one even more preferred embodiment, the piggyBac transposase has an amino acid sequence according to SEQ ID NO: 18 and comprises at least one amino acid substitution (e.g. 1, 2, 3, 4, or 5 amino acid substitution(s)) selected from the group consisting of isoleucine (I) at amino acid position 30 is replaced by alanine (A) (I30A), glutamine (Q) at amino acid position 118 is replaced by proline (P) (Q118P), methionine (M) at amino acid position 185 is replaced by valine (V) (M185V), methionine (M) at amino acid position 282 is replaced by leucine (L) (M282L), and asparagine (N) at amino acid position 538 is replaced by arginine (R) (N538R), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said amino acid sequence, wherein said variant comprises at least one amino acid substitution (e.g. at least 1, 2, 3, 4, or 5 amino acid substitution(s)) selected from the group consisting of isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

In one still more preferred embodiment, the piggyBac transposase has an amino acid sequence according to SEQ ID NO: 18 and comprises the following amino acid substitutions:

isoleucine (I) at amino acid position 30 is replaced by alanine (A) (I30A), glutamine (Q) at amino acid position 118 is replaced by proline (P) (Q118P), methionine (M) at amino acid position 185 is replaced by valine (V) (M185V), methionine (M) at amino acid position 282 is replaced by leucine (L) (M282L), and asparagine (N) at amino acid position 538 is replaced by arginine (R) (N538R), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said amino acid sequence, wherein said variant comprises the following amino acid substitutions:

isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

Thus, the piggyBac transposase specifically has an amino acid sequence according to SEQ ID NO: 20 comprising alanine (A) at amino acid position 30, proline (P) at amino acid position 118, valine (V) at amino acid position 185, leucine (L) at amino acid position 282 and arginine (R) at amino acid position 538, or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said amino acid sequence, wherein said variant comprises alanine (A) at amino acid position 30 or at an amino acid position corresponding thereto, proline (P) at amino acid position 118 or at an amino acid position corresponding thereto, amino acid valine (V) at amino acid position 185 or at an amino acid position corresponding thereto, leucine (L) at amino acid position 282 or at an amino acid position corresponding thereto and arginine (R) at amino acid position 538 or at an amino acid position corresponding thereto. This piggyBac transposase has a nucleotide sequence according to SEQ ID NO: 19.

In one most preferred embodiment, the piggyBac transposase has an amino acid sequence according to SEQ ID NO: 18 and comprises the following amino acid substitutions:

isoleucine (I) at amino acid position 30 is replaced by alanine (A) (I30A), methionine (M) at amino acid position 282 is replaced by leucine (L) (M282L), and asparagine (N) at amino acid position 538 is replaced by arginine (R) (N538R), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said amino acid sequence, wherein said variant comprises the following amino acid substitutions:

isoleucine (I) at amino acid position 30 or at an amino acid position corresponding thereto is replaced by alanine (A) (I30A), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R).

Thus, the piggyBac transposase specifically has an amino acid sequence according to SEQ ID NO: 22 comprising alanine (A) at amino acid position 30, leucine (L) at amino acid position 282 and arginine (R) at amino acid position 538, or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said amino acid sequence, wherein said variant comprises alanine (A) at amino acid position 30 or at an amino acid position corresponding thereto, leucine (L) at amino acid position 282 or at an amino acid position corresponding thereto and arginine (R) at amino acid position 538 or at an amino acid positon corresponding thereto. This piggyBac transposase has a nucleotide sequence according to SEQ ID NO: 21.

The piggyBac transpose, fragment or derivative thereof according to the first aspect has an improved transposase function, in particular an improved activity/ability to mediate nucleotide sequence, e.g. DNA, excision and/or insertion, compared to transposases described in art (e.g. wild-type/naturally occurring transposases). In particular, the above-mentioned piggyBac transposase or fragment or derivative thereof is able to mobilize a transposon, e.g. the transposable element described herein, from one genomic location to another with a higher effectivity than transposases described in art (e.g. wild-type/naturally occurring transposases). Thus, the piggyBac transpose, fragment or derivative thereof according to the first aspect can also be designated as hyperactive piggyBac transpose, fragment or derivative thereof.

In one further preferred embodiment, the polypeptide comprises at least one heterologous chromatin reader element (CRE). A polypeptide comprising a hyperactive transposase, or a fragment, or a derivative thereof and at least one chromatin reader element (CRE) allows the targeting of a transposable element, in particular the transposable element of the present invention, to random positions in the genome with high transcriptional activity. In other words, a polypeptide comprising a transposase or a fragment or a derivative thereof and at least one chromatin reader element allows the targeting of active chromatin. The result of this targeting process is the integration of a transposable element, in particular the transposable element of the present invention, including a polynucleotide of interest (e.g. encoding a protein or virus particle) via the transposase or fragment or derivative thereof in transcriptionally active chromatin. This, in turn, allows the generation of high producer cell lines for the production of proteins (e.g. therapeutic proteins) or biopharmaceutical products based on virus particles.

The at least one heterologous chromatin reader element (CRE) may be connected to the transposase or fragment or derivative thereof, preferably via a linker. In particular, the at least one heterologous CRE may be connected to the N-terminus and/or C-terminus of the transposase, preferably via a linker.

In one more preferred embodiment, the at least one heterologous chromatin reader element (CRE) is at least one heterologous chromatin reader domain (CRD). The at least one heterologous chromatin reader domain (CRD) may be connected to the transposase or fragment or derivative thereof, preferably via a linker. In particular, the at least one heterologous CRD may be connected to the N-terminus and/or C-terminus of the transposase, preferably via a linker. Preferably, the CRD recognises histone methylation degree and/or acetylation state of histones. More preferably, the CRD is a plant homeodomain (PHD) type zinc finger. Even more preferably, the PHD type zinc finger is a transcription initiation factor TFIID subunit 3 PHD.

In one alternative more preferred embodiment, the at least one heterologous chromatin reader element (CRE) is an artificial CRE.

Preferably, the artificial CRE recognises histone tails with specific methylated and/or acetylated sites. More preferably, the artificial CRE is selected from the group consisting of a micro antibody, a single chain antibody, an antibody fragment, an affibody, an affilin, an anticalin, an atrimer, a DARPin, a FN2 scaffold, a fynomer, and a Kunitz domain.

In one also (alternative or additional) preferred embodiment, the polypeptide further comprises at least one heterologous DNA binding domain (e.g. at least 1 or 2 DNA binding domain(s)).

In one also (alternative or additional) preferred embodiment, the polypeptide further comprises a heterologous nuclear localization signal (NLS). The NLS may form the N-terminus or the C-terminus of the transposase/polypeptide.

In one more preferred embodiment, the polypeptide comprises the transposase or fragment or derivative thereof as described above, at least one heterologous chromatin reader element (CRE), and at least one heterologous DNA binding domain.

In one even more preferred embodiment, the polypeptide comprises the transposase or fragment or derivative thereof as described above, at least one heterologous chromatin reader element (CRE), at least one heterologous DNA binding domain, and a heterologous nuclear localization signal (NLS).

In a second aspect, the present invention relates to a polynucleotide encoding the polypeptide according to the first aspect. Said polynucleotide is preferably DNA or RNA such as mRNA.

In a third aspect, the present invention relates to a vector comprising the polynucleotide according to the second aspect. The terms "vector" and "plasmid" can interchangeable be used herein. The vector may be a viral or non-viral vector. Preferably, the vector is an expression vector. In some embodiments the vector is a minicircle. The expression of the polynucleotide encoding the polypeptide according to the first aspect is preferably controlled by expression control sequences. Expression control sequences may be sequences which control the transcription, e.g. promoters, enhancers, UCOE or MAR elements, polyadenylation signals, post-transcriptionally active elements, e.g. RNA stabilising elements, RNA transport elements and translation enhancers. Said expression control sequences are known to the skilled person. For example, as promoters, CMV or PGK promoters may be used.

In a fourth aspect, the present invention relates to a transposable element comprising a piggyBac or piggyBac-like left repeat sequence and left internal repeat sequence, wherein the left internal repeat sequence comprises at least one nucleotide modification, wherein the at least one nucleotide modification increases the homology of the left internal repeat sequence to the left repeat sequence.

Preferably, the at least one nucleotide modification is selected from the group consisting of a nucleotide substitution (e.g. at least 1, 2, 3, or 4 nucleotide substitution(s)), a nucleotide deletion (e.g. at least 1, 2, 3, or 4 nucleotide deletion(s)), a nucleotide addition (e.g. at least 1, 2, 3, or 4 nucleotide addition(s)), and a nucleotide insertion (e.g. at least 1, 2, 3, or 4 nucleotide insertion(s)), or is a combination thereof.

The piggyBac left repeat sequence and/or left-internal repeat sequence is (are) preferably from *Trichoplusia ni*. The piggyBac-like left repeat sequence and/or left-internal repeat sequence is (are) preferably selected from the group consisting of *Xenopus tropicalis*, *Bombyx mori* (silk worm), and *Myotis lucifugus*.

In one preferred embodiment, the piggyBac left internal repeat sequence has a nucleotide sequence according to SEQ ID NO: 1 and comprises at least one nucleotide substitution (e.g. at least 1, 2, 3, or 4 substitution(s)) selected from the group consisting of adenosine (A) at nucleotide position 3 is replaced by cytidine (C) (A3C), adenosine (A) at nucleotide position 9 is replaced by thymidine (T) (A9T), adenosine (A) at nucleotide position 10 is replaced by thymidine (T) (A10T), and guanosine (G) at nucleotide position 12 is replaced by thymidine (T) (G12T), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1, 2, 3, or 4 substitution(s)) selected from the group consisting of adenosine (A) at nucleotide position 3 or at a nucleotide position corresponding thereto is replaced by cytidine (C) (A3C), adenosine (A) at nucleotide position 9 or at a nucleotide position corresponding thereto is replaced by thymidine (T) (A9T), adenosine (A) at nucleotide position 10 or at a nucleotide position corresponding thereto is replaced by thymidine (T) (A10T), and guanosine (G) at nucleotide position 12 or at a nucleotide position corresponding thereto is replaced by thymidine (T) (G12T).

In one alternative preferred embodiment, the piggyBac-like left internal repeat sequence has a nucleotide sequence according to SEQ ID NO: 2 and comprises a nucleotide insertion, wherein adenosine (A) is introduced between nucleotide positions 7 and 8, or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises a nucleotide insertion, wherein adenosine (A) is introduced between nucleotide positions 7 and 8 or between nucleotide positions corresponding thereto.

In one alternative preferred embodiment the piggyBac-like left internal repeat sequence has a nucleotide sequence according to SEQ ID NO: 3 and comprises at least one nucleotide substitution (e.g. at least 1 or 2 substitution(s)) selected from the group consisting of guanosine (G) at nucleotide position 7 is replaced by cytidine (C) (G7C), and thymidine (T) at nucleotide position 9 is replaced by cytidine (C) (T9C), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1 or 2 substitution (s)) selected from the group consisting of guanosine (G) at nucleotide position 7 or at a nucleotide position corresponding thereto is replaced by cytidine (C) (G7C), and thymidine (T) at nucleotide position 9 or at a nucleotide position corresponding thereto is replaced by cytidine (C) (T9C).

In one alternative preferred embodiment the piggyBac-like left internal repeat sequence has a nucleotide sequence according to SEQ ID NO: 4 and comprises a nucleotide substitution, wherein thymidine (T) at nucleotide position 7 is replaced by adenosine (A) (T7A), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises a nucleotide substitution, wherein thymidine (T) at nucleotide position 7 or at a nucleotide position corresponding thereto is replaced by adenosine (A) (T7A).

In one alternative preferred embodiment the piggyBac-like left internal repeat sequence has a nucleotide sequence according to SEQ ID NO: 5 and comprises at least one nucleotide substitution (e.g. at least 1 or 2 substitution(s)) selected from the group consisting of guanosine (G) at nucleotide position 6 is replaced by thymidine (T) (G6T), and thymidine (T) at nucleotide position 14 is replaced by guanosine (G) (T14G), or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1 or 2 substitution (s)) selected from the group consisting of guanosine (G) at nucleotide position 6 or at a nucleotide position corresponding thereto is replaced by thymidine (T) (G6T), and thymidine (T) at nucleotide position 14 or at a nucleotide position corresponding thereto is replaced by guanosine (G) (T14G).

In one further preferred embodiment, the piggyBac or piggyBac-like left repeat sequence has a nucleotide sequence selected from the group consisting of SEQ ID NO: 23 to SEQ ID NO: 27 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence.

It should be noted that the piggyBac or piggyBac-like left repeat sequence and the piggyBac or piggyBac-like left internal repeat sequence are preferably comprised in/part of a 5'-transposon end sequence. In this respect, it is preferred that a piggyBac left repeat sequence and a piggyBac left-internal repeat sequence are comprised/combined together. It is also preferred that a piggyBac-like left repeat sequence and a piggyBac-like left-internal repeat sequence are comprised/combined together. Thus, in one more preferred embodiment, the 5'-transposon end sequence comprises (i) the piggyBac left repeat sequence having a nucleotide sequence according to SEQ ID NO: 23 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, and the piggyBac left internal repeat sequence having a nucleotide sequence according to SEQ ID NO: 1 and comprising at least one nucleotide substitution (e.g. at least 1, 2, 3, or 4 substitution(s)) selected from the group consisting of A3C, A9T, A10T, and G12T or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1, 2, 3, or 4 substitution (s)) selected from the group consisting of A3C, A9T, A10T, and G12T (or at positions corresponding thereto), (ii) the piggyBac-like left repeat sequence having a nucleotide sequence according to SEQ ID NO: 24 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, and the piggyBac-like left internal repeat sequence having a nucleotide sequence according to SEQ ID NO: 2 and comprising an adenosine insertion between nucleotide positions 7 and 8 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises an adenosine insertion between nucleotide positions 7 and 8 (or between nucleotide positions corresponding thereto), (iii) the piggyBac-like left repeat sequence having a nucleotide sequence according to SEQ ID NO: 25 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, and the piggyBac-like left internal repeat sequence having a nucleotide sequence according to SEQ ID NO: 3 and comprising at least one nucleotide substitution (e.g. at least 1 or 2 substitution(s)) selected from the group consisting of G7C and T9C or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1 or 2 substitution(s)) selected from the group consisting of G7C and T9C (or at positions corresponding thereto), (iv) the piggyBac-like left repeat sequence having a nucleotide sequence according to SEQ ID NO: 26 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, and the piggyBac-like left internal repeat sequence having a nucleotide sequence according to SEQ ID NO: 4 and comprising the nucleotide substitution T7A or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises the nucleotide substitution T7A (or at a position corresponding thereto), (v) the piggyBac-like left repeat sequence having a nucleotide sequence according to SEQ ID NO: 27 or a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, and the piggyBac-like left internal repeat sequence having a nucleotide sequence according to SEQ ID NO: 5 and comprising at least one nucleotide substitution (e.g. at least 1 or 2 substitution(s)) selected from the group consisting of G6T and T14G or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said variant comprises at least one nucleotide substitution (e.g. at least 1 or 2 substitution(s)) selected from the group consisting of G6T and T14G (or at positions corresponding thereto).

The piggyBac or piggyBac-like left repeat sequence and the piggyBac or piggyBac-like left internal repeat sequence may be combined/connected with each other by natural transposable element sequences or by non-naturally transposable element sequences, e.g. by (heterologous) linker sequences.

In one alternative more preferred embodiment, the 5'-transposon end sequence has (i) a nucleotide sequence according to SEQ ID NO: 6 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said nucleotide sequence or variant thereof encompasses the nucleotide sequence according to SEQ ID NO: 1 comprising at least one nucleotide substitution (e.g. at least 1, 2, 3, or 4 substitution(s)) selected from the group consisting of A3C, A9T, A10T, and G12T, (ii) a nucleotide sequence according to SEQ ID NO: 7 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said nucleotide sequence or variant thereof encompasses the nucleotide sequence according to SEQ ID NO: 2 comprising an adenosine insertion between nucleotide positions 7 and 8, (iii) a nucleotide sequence according to SEQ ID NO: 8 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said nucleotide sequence or variant thereof encompasses the nucleotide sequence according to SEQ ID NO: 3 comprising at least one nucleotide substitution (e.g. at least 1 or 2 substitution(s)) selected from the group consisting of G7C and T9C, (iv) a nucleotide sequence according to SEQ ID NO: 9 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said nucleotide sequence or variant thereof encompasses the nucleotide sequence according to SEQ ID NO: 4 comprising the nucleotide substitution T7A, or (v) a nucleotide sequence according to SEQ ID NO: 10 or is a variant thereof which is at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, identical to said nucleotide sequence, wherein said nucleotide sequence or variant thereof encompasses the nucleotide sequence according to SEQ ID NO: 5 comprising at least one nucleotide substitution (e.g. at least 1 or 2 substitution(s)) selected from the group consisting of G6T and T14G.

The left internal repeat sequences comprising the nucleotide modifications described above may also be designated as artificial/modified left internal repeat sequences. A particularly preferred artificial/modified left internal repeat sequence has a nucleotide sequence according to SEQ ID NO: 28. In addition, the 5'-transposon end sequences comprising the nucleotide modifications described above may also be designated as artificial/modified 5'-transposon end sequences. A particularly preferred artificial/modified 5'-transposon end sequence has a nucleotide sequence according to SEQ ID NO: 15 or SEQ ID NO: 16.

It should be noted that the transposable element preferably comprises a piggyBac or piggyBac-like 3'-transposon end sequence. This is preferably a wild-type sequence. A preferred 3'-transposon end sequence has a nucleotide sequence according to SEQ ID NO: 12 or SEQ ID NO: 14. Thus, in one even more preferred embodiment, the transposable element comprises a piggyBac or piggyBac-like 5'-transposon end sequence comprising the above-mentioned piggyBac or piggyBac-like left internal repeat sequences and the above-mentioned piggyBac or piggyBac-like left repeat sequences as well as a piggyBac or piggyBac-like 3'-transposon end sequence.

It should be noted that the transposable element preferably comprises at least one polynucleotide of interest, or at least one cloning site for inserting at least one polynucleotide of interest.

In particular, the at least one polynucleotide of interest is operably linked to the piggyBac or piggyBac-like 5'-transposon end sequence and to the piggyBac or piggyBac-like 3'-transposon end sequence, or the at least one cloning site for inserting the at last one polynucleotide of interest is located between the pig-gyBac or piggyBac-like 5'-transposon end sequence and the piggyBac or piggyBac-like 3'-transposon end sequence.

The at least one polynucleotide of interest may be operably linked to the piggyBac or piggyBac-like 5'-transposon end sequence and to the piggyBac or piggyBac-like 3'-transpo-son end sequence by natural transposable element sequences or by non-naturally transposable element sequences, e.g. by (heterologous) linker sequences.

The at least one polynucleotide of interest is preferably selected from the group consisting of a polynucleotide encoding a polypeptide, a non-coding polynucleotide, a polynucleotide comprising a promoter sequence, a poly-nucleotide encoding a mRNA, a polynucleotide encoding a tag, and a viral polynucleotide.

The polynucleotide of interest may encode a therapeutically active polypeptide, e.g. an antibody, an antibody fragment, a monoclonal antibody, a virus protein, a virus protein fragment, an antigen, a hormone. The polypeptide may be used for gene therapy, e.g. of monogenic diseases. In this case, the polynucleotide encoding the polypeptide is oper-ably linked with a tissue-specific promoter. The polypeptide may also be used for cell therapy, in particularly ex vivo. The cells may be pluripotent stem cells (iPSC), human embry-onic stem (hES) cells, human hematopoietic stem cells (HSCs), or human T lymphocytes. The non-coding poly-nucleotide may be useful in the targeted disruption of a gene. The polynucleotide comprising promoter sequences may allow the activation of gene expression if the transposon inserts close to an endogenous gene. The polynucleotide may be transcribed into mRNA or a functional noncoding RNA e.g. a shRNA or gRNA. The polynucleotide may comprise a sequence tag to identify the insertion site of the transposable element. The viral polynucleotide may be used for the production of biopharmaceutical products based on virus particles.

The expression of the polynucleotide of interest is preferably controlled by expression control sequences. Expression con-trol sequences may be sequences which control the tran-scription, e.g. promoters, enhancers, UCOE or MAR ele-ments, polyadenylation signals, post-transcriptionally active elements, e.g. RNA stabilising elements, RNA transport elements and translation enhancers. Said expression control sequences are known to the skilled person. For example, as promoters, CMV or PGK promoters may be used.

A preferred structure of the transposable element comprising a polynucleotide of interest (GOI=gene of interest) is shown in FIG. 2a.

Thus, in one still more preferred embodiment, the trans-posable element comprises a piggyBac or piggyBac-like 5'-transposon end sequence comprising the above-men-tioned piggyBac or piggyBac-like left internal repeat sequences and the above-mentioned piggyBac or piggyBac-like left repeat sequences, at least one polynucleotide of interest, and a piggyBac or piggyBac-like 3'-transposon end sequence. Preferred structures of the transposable element comprising a polynucleotide of interest (GOI=gene of inter-est) are shown in FIG. 2b.

Alternatively, the transposable element comprises a piggy-Bac or piggyBac-like 5'-transposon end sequence compris-ing the above-mentioned piggyBac or piggyBac-like left internal repeat sequences and the above-mentioned piggy-Bac or piggyBac-like left repeat sequences, at least one cloning site for inserting the at least one polynucleotide of interest, and a piggyBac or piggyBac-like 3'-transposon end sequence.

It is preferred that the transposable element is circular, is comprised in/part of a plasmid vector, or is comprised in/part of a minicircle DNA vector.

The transposable element and/or the vector comprising the transposable element may further comprise elements that enhance expression (e.g. nuclear export signals, promoters, introns, terminators, enhancers, elements that affect chro-matin structure, RNA export elements, IRES elements, CHYSEL elements, and/or Kozak sequences), selectable marker (e.g. DHFR, puromycine, hygromycin, zeocin, blas-ticidin, and/or neomycin), markers for in vivo monitoring (e.g. GFP or beta-galactosidase), a restriction endonuclease recognition site (e.g. a site for insertion of an exogenous nucleotide sequence such as a multiple cloning site), a recombinase recognition site (e.g. LoxP (recognized by Cre), FRT (recognized by Flp), or AttB/AttP (recognized by PhiC31)), insulators (e.g. MARs or UCOEs), viral replica-tion sequences (e.g. SV40 ori), and/or a sequence compat-ible to a DNA binding domain.

It is also preferred that the transposable element is a piggyBac or piggyBac-like transposable element. It is more preferred that the piggyBac transposable element is from *Trichoplusia ni*. It is alternatively more preferred that the piggyBac-like transposable element is selected from the group consisting of *Xenopus tropicalis, Bombyx mori* (silk worm), and *Myotis lucifugus*.

In a fifth aspect, the present invention relates to a(n) (in vitro or in vivo) method for producing a transgenic cell comprising the steps of:

(i) providing a cell, and
(ii) introducing
    (iia) a transposable element, and
        a polypeptide according to the first aspect, or
        a polynucleotide of according to the second aspect, or
        a vector according to the third aspect, or
    (iib) a transposable element according to the fourth aspect, and
        a transposase or a fragment or a derivative thereof having transposase function, or
        a polynucleotide encoding a transposase or a frag-ment or a derivative thereof having transposase function, or
        a vector comprising a polynucleotide encoding a transposase or a fragment or a derivative thereof having transposase function, or
    (iic) a transposable element according to the fourth aspect, and
        a polypeptide according to the first aspect, or
        a polynucleotide according to the second aspect, or
        a vector according to the third aspect
    into the cell, thereby producing the transgenic cell.

The method may be an in vitro or in vivo method. Preferably, the method is an in vitro method.

In one embodiment, the introduction takes place via electroporation, transfection, injection, lipofection, and/or (viral) infection.

Naturally, a transposable element includes a polynucle-otide encoding a functional transposase that catalyses exci-sion and insertion. The transposable element referred to in (iia), (iib), and (iic) of the above method is, however, devoid of a polynucleotide encoding a functional transposase. This transposable element does not comprise the complete sequence encoding a functional, in particular a naturally occurring, transposase. Preferably, the complete sequence encoding a functional, in particular a naturally occurring, transposase or a portion thereof, is deleted from this transposable element. It may be replaced by at least one polynucleotide of interest (see below).

The transposase or a fragment or a derivative thereof having transposase function is provided in the above method in trans, e.g. as a polypeptide such as a polypeptide according to the first aspect, as a polynucleotide such as a polynucleotide according to the second aspect, or comprised in a vector such as a vector according to the third aspect.

The introduction of the transposable element referred to in (iia), (iib), and (iic) of the above method may take place via electroporation, transfection, injection, lipofection, or (viral) infection. This transposable element may be introduced transiently or stably into the cell. In the first case, the transposable element is introduced as extrachromosomal element, e.g. as linear DNA molecule, plasmid DNA, episomal DNA, DNA minicircle, viral DNA, or viral RNA. In the second case, the transposable element is stably introduced/inserted into the genome of the cell. Preferably, the transposable element is transiently introduced into the cell. More preferably, the transposable element is comprised in a vector. The person skilled in the art is well informed about molecular biological techniques, such as microinjection, electroporation or lipofection, for introducing the transposable element into a cell and knows how to perform these techniques.

It is particularly preferred that the transposable element is the transposable element according to the fourth aspect.

The introduction of the polypeptide, polynucleotide, or vector referred to in (iia), (iib), and (iic) of the above method may also take place via electroporation, transfection, injection, lipofection, and/or (viral) infection.

If a polynucleotide is introduced into the cell, the polynucleotide is subsequently transcribed and translated into the polypeptide in the cell. If a vector comprising the polynucleotide is introduced into the cell, the polynucleotide is subsequently transcribed from the vector and translated into the polypeptide in the cell. The polynucleotide may be DNA or RNA such as mRNA. Also viral DNA or RNA may be introduced. The polynucleotide may be introduced transiently or stably into the cell. In the first case, the polynucleotide is introduced as extrachromosomal polynucleotide, e.g. as linear DNA molecule, circular DNA molecule, plasmid DNA, viral DNA, in vitro synthesised/transcribed RNA, or viral RNA. In the second case, the polynucleotide is stably introduced/inserted into the genome of the cell. Preferably, the polynucleotide is transiently introduced into the cell. More preferably, the polynucleotide is comprised in a vector, in particular in an expression vector. The viral DNA or RNA sequences may also be introduced as part of a vector or in form of a vector. It is particularly preferred that the polynucleotide is operably linked to a heterologous promoter allowing the transcription of the transposase, or a fragment or a derivative thereof having transposase function within the cell or from a vector, e.g. expression vector or a vector used for in vitro transcription, comprised in the cell. The person skilled in the art is well informed about molecular biological techniques, such as microinjection, electroporation or lipofection, for introducing polypeptides or nucleic acid sequences encoding polypeptides into a cell and knows how to perform these techniques.

It is particularly preferred that the polypeptide is the polypeptide according to the first aspect, the polynucleotide is the polynucleotide according to the second aspect, or the vector is the vector according to the third aspect.

In one preferred embodiment, the transposable element referred to in (iia), (iib), and (iic) of the above method is comprised in/part of a polynucleotide molecule, preferably a vector. In this case, the polynucleotide referred to in (iia), (iib), and (iic) is also comprised in/part of a polynucleotide molecule, preferably a vector. Thus, it is preferred that the polynucleotide referred to in (iia), (iib), and (iic) of the above method and the transposable element referred to in (iia), (iib), and (iic) of the above method are on separate (different) polynucleotide molecules, preferably (different) vectors.

It is particularly preferred that the transposable element of (iia) is comprised in/part of a polynucleotide molecule, preferably a vector.

In one alternatively preferred embodiment, the transposable element referred to in (iia), (iib), and (iic) of the above method and the polynucleotide referred to in (iia), (iib), and (iic) of the above method are comprised in/part of a (the same) polynucleotide molecule, preferably a vector.

It is particularly preferred that the transposable element of (iia) and the polynucleotide according to the second aspect are comprised in/part of a polynucleotide molecule, preferably a vector.

The transposable element referred to in (iia), (iib), and (iic) of the above method retains sequences that are required for mobilization by the transposase provided in trans. These are the repetitive sequences at each end of the transposable element containing the binding sites for the transposase allowing the excision from the genome. Thus, in one further preferred embodiment, the transposable element referred to in (iia), (iib), and (iic) of the above method comprises terminal repeats (TRs). It is particularly preferred that the transposable element of (iia) comprises terminal repeats (TRs). The terminal repeats are preferably terminal inverted repeats (TIRs). In this respect, it should be noted that the transposase provided in trans is specific for the transposable element. In other words, the transposable element is specifically recognized by the transposase.

In one further (alternative or additional) preferred embodiment, the transposable element referred to in (iia), (iib), and (iic) of the above method comprises at least one polynucleotide of interest. It is particularly preferred that the transposable element of (iia) comprises at least one polynucleotide of interest.

Preferably, the at least one polynucleotide of interest is flanked by terminal repeats (TRs). More preferably, the terminal repeats are terminal inverted repeats (TIRs). For example, the transposable element referred to in (iia), (iib), and (iic) of the above method comprises a first transposable element-specific terminal repeat and a second transposable element-specific terminal repeat downstream of the first transposable element-specific terminal repeat. The at least one polynucleotide of interest is located between the first transposable element-specific terminal repeat and the second transposable element-specific terminal repeat.

Even more preferably, the at least one polynucleotide of interest is selected from the group consisting of a polynucleotide encoding a polypeptide, a non-coding polynucleotide, a polynucleotide comprising a promoter sequence, a polynucleotide encoding a mRNA, a polynucleotide encoding a tag, and a viral polynucleotide.

The polynucleotide of interest may encode a therapeutically active polypeptide, e.g. an antibody, an antibody fragment, a monoclonal antibody, a virus protein, a virus protein fragment, an antigen, a hormone. The polypeptide may be used for gene therapy, e.g. of monogenic diseases. In this case, the polynucleotide encoding the polypeptide is operably linked with a tissue-specific promoter. The polypeptide may also be used for cell therapy, in particularly ex vivo. The cells may be pluripotent stem cells (iPSC), human embryonic stem (hES) cells, human hematopoietic stem cells (HSCs), or human T lymphocytes. The non-coding polynucleotide may be useful in the targeted disruption of a gene. The polynucleotide comprising promoter sequences may allow the activation of gene expression if the transposon inserts close to an endogenous gene. The polynucleotide may be transcribed into mRNA or a functional noncoding RNA e.g. a shRNA or gRNA. The polynucleotide may comprise a sequence tag to identify the insertion site of the transposable element. The viral polynucleotide may be used for the production of biopharmaceutical products based on virus particles.

The expression of the polynucleotide of interest is preferably controlled by expression control sequences. Expression control sequences may be sequences which control the transcription, e.g. promoters, enhancers, UCOE or MAR elements, polyadenylation signals, post-transcriptionally active elements, e.g. RNA stabilising elements, RNA transport elements and translation enhancers. Said expression control sequences are known to the skilled person. For example, as promoters, CMV or PGK promoters may be used.

The transposable element and/or the vector comprising the transposable element referred to in (iia), (iib), and (iic) of the above method may further comprise elements that enhance expression (e.g. nuclear export signals, promoters, introns, terminators, enhancers, elements that affect chromatin structure, RNA export elements, IRES elements, CHYSEL elements, and/or Kozak sequences), selectable marker (e.g. DHFR, puromycine, hygromycin, zeocin, blasticidin, and/or neomycin), markers for in vivo monitoring (e.g. GFP or beta-galactosidase), a restriction endonuclease recognition site (e.g. a site for insertion of an exogenous nucleotide sequence such as a multiple cloning site), a recombinase recognition site (e.g. LoxP (recognized by Cre), FRT (recognized by Flp), or AttB/AttP (recognized by PhiC31)), insulators (e.g. MARs or UCOEs), viral replication sequences (e.g. SV40 ori), and/or a sequence compatible to a DNA binding domain, in particular for targeting via an additional binding molecule with chromatin reader domain and DNA binding domain properties ("bridging").

In the above method, not only one but also more than one transposable element may be inserted into the cell. The transposable elements may differ from each other, e.g. as they comprise different polynucleotides of interest. This is specifically desired in cases were two ORFs encoding antibody heavy chains (HC) or antibody light chains (LC) have to be introduced into the cell. In this case, the two or more ORFs are comprised in the same or on separate transposable elements, preferably on separate transposable elements.

In one also (alternative or additional) preferred embodiment, the transposable element referred to in (iia), (iib), and (iic) of the above method is a DNA transposable element. Said DNA transposable element preferably comprises terminal inverted repeats (TIRs). It is particularly preferred that the transposable element of (iia) is a DNA transposable element and that this DNA transposable element preferably comprises terminal inverted repeats (TIRs). The DNA transposable element may be a piggyBac or piggyBac-like transposable element.

It is particularly preferred that the transposable element of (iia) of the above method is selected from the group consisting of a wild-type piggyBac transposable element, a hyperactive piggyBac transposable element, a wild-type piggyBac-like transposable element, and a hyperactive piggyBac-like transposable element. It is particularly more preferred that the piggyBac-like transposable element is selected from the group consisting of piggyBat transposable element, piggyBac-like transposable element from *Xenopus tropicalis*, piggyBac-like transposable element from *Bombyx mori*, and piggyBac-like transposable element from *Myotis lucifugus*. It is also particularly more preferred that the piggyBac transposable element is from *Trichoplusia ni*.

Conservative DNA-based transposable elements move by a cut-and-paste mechanism. This requires a transposase, inverted repeats at the ends of the transposable element and a target sequence on the new host DNA molecule. The transposase is provided in the above mentioned method in trans. It catalysis the excision of the transposable element from the current location and the integration of the excised transposable element into the genome of a cell. In the cut-and-paste mechanism, the transposase specifically binds to the inverted terminal repeats of the transposable element and cuts the transposable element out of the current location, e.g. vector. The transposase then locates the transposable element, cuts the target DNA backbone and then inserts the transposable element. Usually, two transposase monomers are involved in the excision of the transposable element, one transposase monomer at each end of the transposable element. Finally, the transposase dimer in complex with the excised transposable element reintegrates the transposable element in the DNA of a cell.

It is particularly preferred that the transposase or fragment or derivative thereof of (iib) of the above method is selected from the group consisting of a wild-type piggyBac transposase or fragment or derivative thereof, a hyperactive piggyBac transposase or fragment or derivative thereof, a wild-type piggyBac-like transposase or fragment or derivative thereof, and a hyperactive piggyBac-like transposase or fragment or derivative thereof. It is particularly more preferred that the piggyBac-like transposase or fragment or derivative thereof is selected from the group consisting of piggyBat transposase or fragment or derivative thereof, piggyBac-like transposase or fragment or derivative thereof from *Xenopus tropicalis*, piggyBac-like transposase or fragment or derivative thereof from *Bombyx mori*, and piggyBac-like transposase or fragment or derivative thereof from *Myotis lucifugus*. It is also particularly more preferred that the piggyBac transposase or fragment or derivative thereof is from *Trichoplusia ni*.

It is further particularly preferred that the transposase or fragment or derivative thereof of (iib) of the above method is attached/fused to at least one heterologous chromatin reader element (CRE). The at least one heterologous chromatin reader element (CRE) may be connected to the transposase or fragment or derivative thereof, preferably via a linker. In particular, the at least one heterologous CRE may be connected to the N-terminus and/or C-terminus of the transposase, preferably via a linker.

It is particularly more preferred that the at least one heterologous chromatin reader element (CRE) is at least one heterologous chromatin reader domain (CRD). The at least one heterologous chromatin reader domain (CRD) may be connected to the transposase or fragment or derivative thereof, preferably via a linker. In particular, the at least one heterologous CRD may be connected to the N-terminus and/or C-terminus of the transposase, preferably via a linker. Preferably, the CRD recognises histone methylation degree and/or acetylation state of histones. More preferably, the CRD is a plant homeodomain (PHD) type zinc finger. Even more preferably, the PHD type zinc finger is a transcription initiation factor TFIID subunit 3 PHD. It is alternatively particularly more preferred that the at least one heterologous chromatin reader element (CRE) is an artificial CRE.

Preferably, the artificial CRE recognises histone tails with specific methylated and/or acetylated sites. More preferably, the artificial CRE is selected from the group consisting of a micro antibody, a single chain antibody, an antibody fragment, an affibody, an affilin, an anticalin, an atrimer, a DARPin, a FN2 scaffold, a fynomer, and a Kunitz domain.

The cell may be a prokaryotic or an eukaryotic cell. Preferably, the cell is an eukaryotic cell. More preferably, the eukaryotic cell is a vertebrate, a yeast, a fungus, or an insect cell. The vertebrate cell may be a mammalian, a fish, an amphibian, a reptilian cell or an avian cell. The avian cell may be a chicken, quail, goose, or duck cell such as a duck retina cell or duck somite cell. Even more preferably, the vertebrate cell is a mammalian cell. Most preferably, the mammalian cell is selected from the group consisting of a Chinese hamster ovary (CHO) cell (e.g. CHO-K1/CHO-S/CHO-DUXB11/CHO-DG44 cell), a human embryonic kidney (HEK293) cell, a HeLa cell, a A549 cell, a MRCS cell, a WI38 cell, AGE1.CR cell, a BHK cell, and a Vero cell. The cell may be an isolated cell (such as in a cell culture or in a cell line, e.g. stable cell line). The cell may also be a cell of a tissue outside of an organism. The transgenic cell may, however, subsequently be inserted into an organism. Insertion of the transgenic cell into the organisms may be effected by infusion or injection or further means well known to the person skilled in the art.

The cell may also be part of/comprised in an organism, e.g. eukaryotic multicellular organism. In this case, the insertion of the transposable element, a polypeptide, polynucleotide, a vector referred to in (iia), (iib), and (iic) of the above method is effected in vivo. In vivo delivery can be accomplished by injection (either locally or systemically). The polynucleotide/transposable element can be, for example, in the form of naked DNA, DNA complexed with liposomes, PEI or other condensing agents, or can be incorporated into infectious particles (viruses or virus-like particles). Polynucleotide/transposable element delivery can also be done using electroporation or with gene guns or with aerosols.

Said organism may be a prokaryotic or an eukaryotic organism. Preferably, said organism is an eukaryotic organism. More preferably, said organism may be a fungus, an insect, or a vertebrate. The vertebrate may be a bird (e.g. a chicken, quail, goose, or duck), a canine, a mustela, a rodent (e.g. a mouse, rat or hamster), an ovine, a caprine, a pig, a bat (e.g. a megabat or microbat) or a human/non-human primate (e.g. a monkey or a great ape). Most preferably the organism is a mammal such as a mouse, a rat, a pig, or a human/non-human primate.

In the sixth aspect, the present invention relates to a cell, in particular transgenic cell, obtainable/producible by the method of the fifth aspect.

In a seventh aspect, the present invention relates to the use of a cell, in particular transgenic cell, of the sixth aspect for the production of a protein or virus. The proteins may be therapeutic proteins. The virus may be a vector (viral vector).

In an eighth aspect, the present invention relates to a kit comprising
    (i) a transposable element, and
        a polypeptide according to the first aspect, or
        a polynucleotide according to the second aspect, or
        a vector according to the third aspect; or
    (ii) a transposable element according to the fourth aspect, and a transposase or a fragment or a derivative thereof having transposase function, or
        a polynucleotide encoding a transposase or a fragment or a derivative thereof having transposase function, or
        a vector comprising a polynucleotide encoding a transposase or a fragment or a derivative thereof having transposase function; or
    (iii) a transposable element according to the fourth aspect, and
        a polypeptide according to the first aspect, or
        a polynucleotide according to the second aspect, or
        a vector according to the third aspect.

The transposable element referred to in (i), (ii), and (iii) is an independent or a distinct component of the kit. The transposable element referred to in (i), (ii), and (iii) may be provided with the kit/comprised in the kit as a linear DNA molecule, plasmid DNA, episomal DNA, minicircle DNA, viral DNA, or viral RNA. Preferably, the transposable element according to the fourth aspect is provided with the kit/comprised in the kit.

The transposable element referred to in (i), (ii), and (iii) which is provided with the kit/comprised in the kit is devoid of a polynucleotide encoding a functional transposase. The transposable element does not comprise the complete sequence encoding a functional, preferably a naturally occurring, transposase. Preferably, the complete sequence encoding a functional, in particular a naturally occurring, transposase or a portion thereof, is deleted from the transposable element.

The transposase is an independent or a distinct component of the kit. It is provided with the kit/comprised in the kit as polypeptide, polynucleotide, or comprised in a vector. Preferably, the polypeptide is a polypeptide according to the first aspect, the polynucleotide is a polynucleotide according to the second aspect, or the vector comprising the polynucleotide is a vector according to the third aspect.

In one preferred embodiment, the transposable element referred to in (i), (ii), and (iii) of the above kit is comprised in/part of a polynucleotide molecule, preferably a vector. In this case, the polynucleotide referred to in (i), (ii), and (iii) is also comprised in/part of a polynucleotide molecule, preferably a vector. Thus, it is preferred that the polynucleotide referred to in (i), (ii), and (iii) of the above kit and the transposable element referred to in (i), (ii), and (iii) of the above kit are on separate (different) polynucleotide molecules, preferably (different) vectors.

It is particularly preferred that the transposable element of (i) is comprised in/part of a polynucleotide molecule, preferably a vector.

In one alternatively preferred embodiment, the transposable element referred to in (i), (ii), and (iii) of the above kit and the polynucleotide referred to in (i), (ii), and (iii) of the above kit are comprised in/part of a (the same) polynucleotide molecule, preferably a vector.

It is particularly preferred that the transposable element of (i) and the polynucleotide according to the second aspect are comprised in/part of a polynucleotide molecule, preferably a vector.

The transposable element referred to in (i), (ii), and (iii) of the above kit retains sequences that are required for mobilization by the transposase provided in trans. These are the repetitive sequences at each end of the transposable element containing the binding sites for the transposase allowing the excision from the genome. Thus, in one further preferred embodiment, the transposable element referred to in (i), (ii), and (iii) of the above kit comprises terminal repeats (TRs). It is particularly preferred that the transposable element of (i) comprises terminal repeats (TRs). The terminal repeats are preferably terminal inverted repeats (TIRs). In this respect, it should be noted that the transposase provided in trans is specific for the transposable element. In other words, the transposable element is specifically recognized by the transposase.

In one further (alternative or additional) preferred embodiment, the transposable element referred to in (i), (ii), and (iii) of the above kit comprises at least one polynucleotide of interest, or at least one cloning site for inserting at least one polynucleotide of interest.

It is particularly preferred that the transposable element of (i) comprises at least one polynucleotide of interest, or at least one cloning site for inserting at least one polynucleotide of interest.

Preferably, the at least one polynucleotide of interest is flanked by TRs, or the at least one cloning site for inserting the at least one polynucleotide of interest is located between the TRs.

More preferably, the terminal repeats are terminal inverted repeats (TIRs). For example, the transposable element referred to in (i), (ii), and (iii) of the above kit comprises a first transposable element-specific terminal repeat and a second transposable element-specific terminal repeat downstream of the first transposable element-specific terminal repeat. The at least one polynucleotide of interest is located between the first transposable element-specific terminal repeat and the second transposable element-specific terminal repeat.

Even more preferably, the at least one polynucleotide of interest is selected from the group consisting of a polynucleotide encoding a polypeptide, a non-coding polynucleotide, a polynucleotide encoding a tag, and a viral polynucleotide. The polynucleotide of interest may encode a therapeutically active polypeptide, e.g. an antibody, an antibody fragment, a monoclonal antibody, a virus protein, a virus protein fragment, an antigen, a hormone. The polypeptide may be used for gene therapy, e.g. of monogenic diseases. In this case, the polynucleotide encoding the polypeptide is operably linked with a tissue-specific promoter. The polypeptide may also be used for cell therapy, in particularly ex vivo. The cells may be pluripotent stem cells (iPSC), human embryonic stem (hES) cells, human hematopoietic stem cells (HSCs), or human T lymphocytes. The non-coding polynucleotide may be useful in the targeted disruption of a gene. The polynucleotide comprising promoter sequences may allow the activation of gene expression if the transposon inserts close to an endogenous gene. The polynucleotide may be transcribed into mRNA or a functional noncoding RNA e.g. a shRNA or gRNA. The polynucleotide may comprise a sequence tag to identify the insertion site of the transposable element. The viral polynucleotide may be used for the production of biopharmaceutical products based on virus particles.

The expression of the polynucleotide of interest is preferably controlled by expression control sequences. Expression control sequences may be sequences which control the transcription, e.g. promoters, enhancers, UCOE or MAR elements, polyadenylation signals, post-transcriptionally active elements, e.g. RNA stabilising elements, RNA transport elements and translation enhancers. Said expression control sequences are known to the skilled person. For example, as promoters, CMV or PGK promoters may be used.

The transposable element and/or the vector comprising the transposable element referred to in (i), (ii), and (iii) of the above kit may further comprise elements that enhance expression (e.g. nuclear export signals, promoters, introns, terminators, enhancers, elements that affect chromatin structure, RNA export elements, IRES elements, CHYSEL elements, and/or Kozak sequences), selectable marker (e.g. DHFR, puromycine, hygromycin, zeocin, blasticidin, and/or neomycin), markers for in vivo monitoring (e.g. GFP or beta-galactosidase), a restriction endonuclease recognition site (e.g. a site for insertion of an exogenous nucleotide sequence such as a multiple cloning site), a recombinase recognition site (e.g. LoxP (recognized by Cre), FRT (recognized by Flp), or AttB/AttP (recognized by PhiC31)), insulators (e.g. MARs or UCOEs), viral replication sequences (e.g. SV40 ori), and/or a sequence compatible to a DNA binding domain, in particular for targeting via an additional binding molecule with chromatin reader domain and DNA binding domain properties ("bridging").

In the above kit, not only one but also more than one transposable element may be comprised. The transposable elements may differ from each other, e.g. as they comprise different polynucleotides of interest. This is specifically desired in cases were two ORFs encoding antibody heavy chains (HC) or antibody light chains (LC) have to be introduced into the cell. In this case, the two or more ORFs are comprised in the same or on separate transposable elements, preferably on separate transposable elements.

In one also (alternative or additional) preferred embodiment, the transposable element referred to in (i), (ii), and (iii) of the above kit is a DNA transposable element. Said DNA transposable element preferably comprises terminal inverted repeats (TIRs). It is particularly preferred that the transposable element of (i) is a DNA transposable element and that this DNA transposable element preferably comprises terminal inverted repeats (TIRs). The DNA transposable element may be a piggyBac or piggyBac-like transposable element.

It is particularly preferred that the transposable element of (i) of the above kit is selected from the group consisting of a wild-type piggyBac transposable element, a hyperactive piggyBac transposable element, a wild-type piggyBac-like transposable element, and a hyperactive piggyBac-like transposable element. It is particularly more preferred that the piggyBac-like transposable element is selected from the group consisting of piggyBat transposable element, piggyBac-like transposable element from *Xenopus tropicalis*, piggyBac-like transposable element from *Bombyx mori*, and piggyBac-like transposable element from *Myotis lucifugus*. It is also particularly more preferred that the piggyBac transposable element is from *Trichoplusia ni*.

Conservative DNA-based transposable elements move by a cut-and-paste mechanism. This requires a transposase, inverted repeats at the ends of the transposable element and a target sequence on the new host DNA molecule. The transposase is provided in the above mentioned method in trans. It catalysis the excision of the transposable element from the current location and the integration of the excised transposable element into the genome of a cell. In the cut-and-paste mechanism, the transposase specifically binds to the inverted terminal repeats of the transposable element and cuts the transposable element out of the current location, e.g. vector. The transposase then locates the transposable element, cuts the target DNA backbone and then inserts the transposable element. Usually, two transposase monomers are involved in the excision of the transposable element, one transposase monomer at each end of the transposable element. Finally, the transposase dimer in complex with the excised transposable element reintegrates the transposable element in the DNA of a cell.

It is particularly preferred that the transposase or fragment or derivative thereof of (ii) of the above kit is selected from the group consisting of a wild-type piggyBac transposase or fragment or derivative thereof, a hyperactive piggyBac transposase or fragment or derivative thereof, a wild-type piggyBac-like transposase or fragment or derivative thereof, and a hyperactive piggyBac-like transposase or fragment or derivative thereof. It is particularly more preferred that the piggyBac-like transposase or fragment or derivative thereof is selected from the group consisting of piggyBat transposase or fragment or derivative thereof, piggyBac-like transposase or fragment or derivative thereof from *Xenopus tropicalis*, piggyBac-like transposase or fragment or derivative thereof from *Bombyx mori*, and piggyBac-like transposase or fragment or derivative thereof from *Myotis lucifugus*. It is also particularly more preferred that the piggyBac transposase or fragment or derivative thereof is from *Trichoplusia ni*.

It is further particularly preferred that the transposase or fragment or derivative thereof of (ii) of the above kit is attached/fused to at least one heterologous chromatin reader element (CRE). The at least one heterologous chromatin reader element (CRE) may be connected to the transposase or fragment or derivative thereof, preferably via a linker. In particular, the at least one heterologous CRE may be connected to the N-terminus and/or C-terminus of the transposase, preferably via a linker.

It is particularly more preferred that the at least one heterologous chromatin reader element (CRE) is at least one heterologous chromatin reader domain (CRD). The at least one heterologous chromatin reader domain (CRD) may be connected to the transposase or fragment or derivative thereof, preferably via a linker. In particular, the at least one heterologous CRD may be connected to the N-terminus and/or C-terminus of the transposase, preferably via a linker. Preferably, the CRD recognises histone methylation degree and/or acetylation state of histones. More preferably, the CRD is a plant homeodomain (PHD) type zinc finger. Even more preferably, the PHD type zinc finger is a transcription initiation factor TFIID subunit 3 PHD.

It is alternatively particularly more preferred that the at least one heterologous chromatin reader element (CRE) is an artificial CRE.

Preferably, the artificial CRE recognises histone tails with specific methylated and/or acetylated sites. More preferably, the artificial CRE is selected from the group consisting of a micro antibody, a single chain antibody, an antibody fragment, an affibody, an affilin, an anticalin, an atrimer, a DARPin, a FN2 scaffold, a fynomer, and a Kunitz domain.

In one embodiment, the kit is for the generation of a cell, in particular transgenic cell.

In one another embodiment, the kit further comprises instructions on how to generate the cell, in particular transgenic cell. As to preferred cells, it is referred to the fifth aspect of the present invention.

The kit may further comprise a container, wherein the single components of the kit are comprised. The kit may also comprise materials desirable from a commercial and user standpoint including a buffer(s), a reagent(s) and/or a diluent(s).

In ninth aspect, the present invention relates to a targeting system comprising (i) a transposable element, and
  a polypeptide according to the first aspect, or a polynucleotide according to the second aspect, or
  a vector according to the third aspect; or
(ii) a transposable element according to the fourth aspect, and
  a transposase or a fragment or a derivative thereof having transposase function, or
  a polynucleotide encoding a transposase or a fragment or a derivative thereof having transposase function, or
  a vector comprising a polynucleotide encoding a transposase or a fragment or a derivative thereof having transposase function; or
(iii) a transposable element according to the fourth aspect, and
  a polypeptide according to the first aspect, or
  a polynucleotide according to the second aspect, or
  a vector according to the third aspect.

The targeting system may be comprised in/part of a cell or may be introduced into a cell. The introduction of the targeting system into a cell may take place via electroporation, transfection, injection, lipofection, or (viral) infection. The cell may be an isolated cell (such as in cell culture or in cell line, e.g. stable cell line). The cell may also be a cell of a tissue outside of an organism. The cell may further be part of/comprised in an organism, e.g. eukaryotic multicellular organism. In this case, the insertion of the targeting system is effected in vivo.

In one preferred embodiment, the transposable element referred to in (i), (ii), and (iii) of the above targeting system is comprised in/part of a polynucleotide molecule, preferably a vector. In this case, the polynucleotide referred to in (i), (ii), and (iii) is also comprised in/part of a polynucleotide molecule, preferably a vector. Thus, it is preferred that the polynucleotide referred to in (i), (ii), and (iii) of the above targeting system and the transposable element referred to in (i), (ii), and (iii) of the above targeting system are on separate (different) polynucleotide molecules, preferably (different) vectors.

It is particularly preferred that the transposable element of (i) is comprised in/part of a polynucleotide molecule, preferably a vector.

In one alternatively preferred embodiment, the transposable element referred to in (i), (ii), and (iii) of the above targeting system and the polynucleotide referred to in (i), (ii), and (iii) of the above targeting system are comprised in/part of a (the same) polynucleotide molecule, preferably a vector.

It is particularly preferred that the transposable element of (i) and the polynucleotide according to the second aspect are comprised in/part of a polynucleotide molecule, preferably a vector.

The transposable element referred to in (i), (ii), and (iii) of the above targeting system retains sequences that are required for mobilization by the transposase provided in trans. These are the repetitive sequences at each end of the transposable element containing the binding sites for the transposase allowing the excision from the genome. Thus, in one further preferred embodiment, the transposable element referred to in (i), (ii), and (iii) of the above targeting system comprises terminal repeats (TRs). It is particularly preferred that the transposable element of (i) comprises terminal repeats (TRs). The terminal repeats are preferably terminal inverted repeats (TIRs). In this respect, it should be noted that the transposase provided in trans is specific for the transposable element. In other words, the transposable element is specifically recognized by the transposase.

In one further (alternative or additional) preferred embodiment, the transposable element referred to in (i), (ii), and (iii) of the above targeting system comprises at least one polynucleotide of interest. It is particularly preferred that the transposable element of (i) comprises at least one polynucleotide of interest.

Preferably, the at least one polynucleotide of interest is flanked by TRs.

More preferably, the terminal repeats are terminal inverted repeats (TIRs). For example, the transposable element referred to in (i), (ii), and (iii) of the above kit comprises a first transposable element-specific terminal repeat and a second transposable element-specific terminal repeat downstream of the first transposable element-specific terminal repeat. The at least one polynucleotide of interest is located between the first transposable element-specific terminal repeat and the second transposable element-specific terminal repeat.

Even more preferably, the at least one polynucleotide of interest is selected from the group consisting of a polynucleotide encoding a polypeptide, a non-coding polynucleotide, a polynucleotide encoding a tag, and a viral polynucleotide. The polynucleotide of interest may encode a therapeutically active polypeptide, e.g. an antibody, an antibody fragment, a monoclonal antibody, a virus protein, a virus protein fragment, an antigen, a hormone. The polypeptide may be used for gene therapy, e.g. of monogenic diseases. In this case, the polynucleotide encoding the polypeptide is operably linked with a tissue-specific promoter. The polypeptide may also be used for cell therapy, in particularly ex vivo. The cells may be pluripotent stem cells (iPSC), human embryonic stem (hES) cells, human hematopoietic stem cells (HSCs), or human T lymphocytes. The non-coding polynucleotide may be useful in the targeted disruption of a gene. The polynucleotide comprising promoter sequences may allow the activation of gene expression if the transposon inserts close to an endogenous gene. The polynucleotide may be transcribed into mRNA or a functional noncoding RNA e.g. a shRNA or gRNA. The polynucleotide may comprise a sequence tag to identify the insertion site of the transposable element. The viral polynucleotide may be used for the production of biopharmaceutical products based on virus particles.

The expression of the polynucleotide of interest is preferably controlled by expression control sequences. Expression control sequences may be sequences which control the transcription, e.g. promoters, enhancers, UCOE or MAR elements, polyadenylation signals, post-transcriptionally active elements, e.g. RNA stabilising elements, RNA transport elements and translation enhancers. Said expression control sequences are known to the skilled person. For example, as promoters, CMV or PGK promoters may be used.

The transposable element and/or the vector comprising the transposable element referred to in (i), (ii), and (iii) of the above targeting system may further comprise elements that enhance expression (e.g. nuclear export signals, promoters, introns, terminators, enhancers, elements that affect chromatin structure, RNA export elements, IRES elements, CHYSEL elements, and/or Kozak sequences), selectable marker (e.g. DHFR, puromycine, hygromycin, zeocin, blasticidin, and/or neomycin), markers for in vivo monitoring (e.g. GFP or beta-galactosidase), a restriction endonuclease recognition site (e.g. a site for insertion of an exogenous nucleotide sequence such as a multiple cloning site), a recombinase recognition site (e.g. LoxP (recognized by Cre), FRT (recognized by Flp), or AttB/AttP (recognized by PhiC31)), insulators (e.g. MARs or UCOEs), viral replication sequences (e.g. SV40 ori), and/or a sequence compatible to a DNA binding domain, in particular for targeting via an additional binding molecule with chromatin reader domain and DNA binding domain properties ("bridging").

In the above targeting system, not only one but also more than one transposable element may be comprised. The transposable elements may differ from each other, e.g. as they comprise different polynucleotides of interest. This is specifically desired in cases were two ORFs encoding antibody heavy chains (HC) or antibody light chains (LC) have to be introduced into the cell. In this case, the two or more ORFs are comprised in the same or on separate transposable elements, preferably on separate transposable elements.

In one also (alternative or additional) preferred embodiment, the transposable element referred to in (i), (ii), and (iii) of the above targeting system is a DNA transposable element. Said DNA transposable element preferably comprises terminal inverted repeats (TIRs). It is particularly preferred that the transposable element of (i) is a DNA transposable element and that this DNA transposable element preferably comprises terminal inverted repeats (TIRs). The DNA transposable element may be a piggyBac or piggyBac-like transposable element.

It is particularly preferred that the transposable element of (i) of the above targeting system is selected from the group consisting of a wild-type piggyBac transposable element, a hyperactive piggyBac transposable element, a wild-type piggyBac-like transposable element, and a hyperactive piggyBac-like transposable element. It is particularly more preferred that the piggyBac-like transposable element is selected from the group consisting of piggyBat transposable element, piggyBac-like transposable element from *Xenopus tropicalis*, piggyBac-like transposable element from *Bombyx mori*, and piggyBac-like transposable element from *Myotis lucifugus*. It is also particularly more preferred that the piggyBac transposable element is from *Trichoplusia ni*.

It is particularly preferred that the transposase or fragment or derivative thereof of (ii) of the above targeting system is selected from the group consisting of a wild-type piggyBac transposase or fragment or derivative thereof, a hyperactive piggyBac transposase or fragment or derivative thereof, a wild-type piggyBac-like transposase or fragment or derivative thereof, and a hyperactive piggyBac-like transposase or fragment or derivative thereof. It is particularly more preferred that the piggyBac-like transposase or fragment or derivative thereof is selected from the group consisting of piggyBat transposase or fragment or derivative thereof, piggyBac-like transposase or fragment or derivative thereof from *Xenopus tropicalis*, piggyBac-like transposase or fragment or derivative thereof from *Bombyx mori*, and piggyBac-like transposase or fragment or derivative thereof from *Myotis lucifugus*. It is also particularly more preferred that the piggyBac transposase or fragment or derivative thereof is from *Trichoplusia ni*.

It is further particularly preferred that the transposase or fragment or derivative thereof of (ii) of the above targeting system is attached/fused to at least one heterologous chromatin reader element (CRE). The at least one heterologous chromatin reader element (CRE) may be connected to the transposase or fragment or derivative thereof, preferably via a linker. In particular, the at least one heterologous CRE may be connected to the N-terminus and/or C-terminus of the transposase, preferably via a linker.

It is particularly more preferred that the at least one heterologous chromatin reader element (CRE) is at least one heterologous chromatin reader domain (CRD). The at least one heterologous chromatin reader domain (CRD) may be connected to the transposase or fragment or derivative thereof, preferably via a linker. In particular, the at least one heterologous CRD may be connected to the N-terminus and/or C-terminus of the transposase, preferably via a linker. Preferably, the CRD recognises histone methylation degree and/or acetylation state of histones. More preferably, the CRD is a plant homeodomain (PHD) type zinc finger. Even more preferably, the PHD type zinc finger is a transcription initiation factor TFIID subunit 3 PHD.

It is alternatively particularly more preferred that the at least one heterologous chromatin reader element (CRE) is an artificial CRE.

Preferably, the artificial CRE recognises histone tails with specific methylated and/or acetylated sites. More preferably, the artificial CRE is selected from the group consisting of a micro antibody, a single chain antibody, an antibody fragment, an affibody, an affilin, an anticalin, an atrimer, a DARPin, a FN2 scaffold, a fynomer, and a Kunitz domain.

In a further aspect, the present invention relates to a (transgenic) cell comprising a transposable element comprising at least one polynucleotide of interest according to the fourth aspect, and a polypeptide according to the first aspect, a polynucleotide according to the second aspect, or a vector according to the third aspect.

As to further preferred embodiments with respect to the cell and the transposable element, it is referred to the fifth aspect of the present invention.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

FIG. 6: Shows single substitutions and preferred combinations of substitutions of the piggyBac transposase or fragment or derivative thereof. At least one of the following substitutions is present: I30A, Q118P, M185V, M282L, and/or N538R.

EXAMPLES

The examples given below are for illustrative purposes only and do not limit the invention described above in any way.

Example 1

Gene Optimization, Synthesis and Construction of the Transposase Expression Plasmids The amino acid sequences of piggyBac wt transposase (*Trichoplusia ni*; GenBank accession number #AAA87375.2; SEQ ID NO: 18 [Virology 172(1) 156-169 1989]) and hyperactive variants thereof (SEQ ID NO: 20 and SEQ ID NO: 22) were reverse translated.

Figure 1:
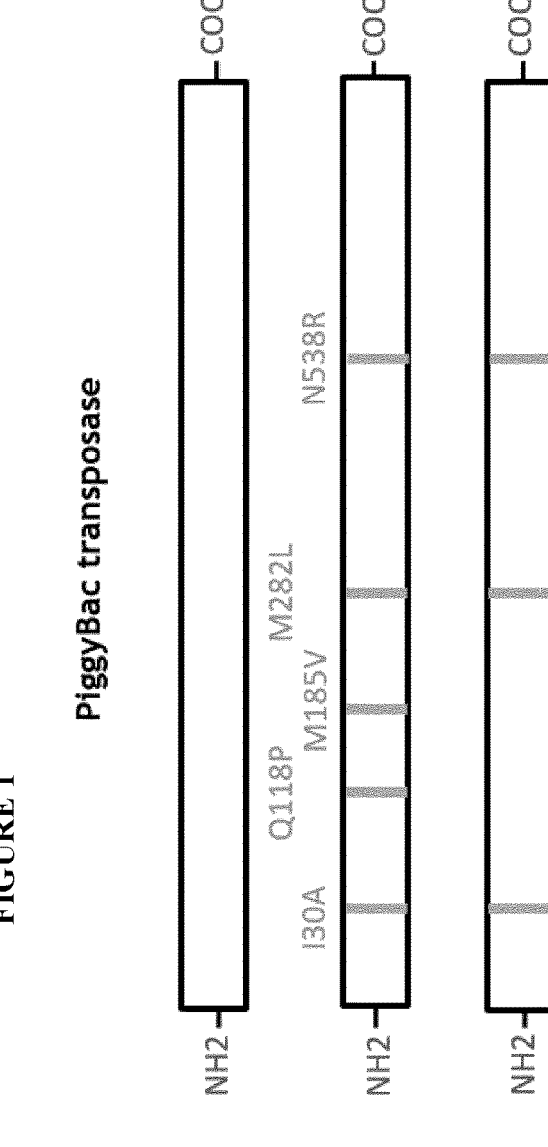
FIG. 1: Tested variants of hyperactive piggyBac transposase. PBw: wild-type (wt) PiggyBac transposase, *Trichoplusia ni*, GenBank accession number #AAA87375.2; haPB1: transposase mutated in 130A, Q118P, M185V, M282L, and N538R compared to wt piggyBac transposase; haPB2: transposase mutated in 130A, M282L, and N538R compared to wt piggyBac transposase; The nucleotide sequences and the corresponding amino acid sequences are listed under SEQ ID NO: 17 and SEQ ID NO: 18 for PBw, SEQ ID NO: 19 and SEQ ID NO: 20 for haPB1 and SEQ ID NO: 21 and SEQ ID NO: 22 for haPB2.

The nucleotide sequences were optimized by knockout of cryptic splice sites and RNA destabilizing sequence elements, optimized for increased RNA stability and adapted to match the requirements of CHO cells (*Cricetulus griseus*) regarding the codon usage. The nucleotide sequences were synthesized by GeneArt Gene Synthesis (Life technologies) and used to generate the constructs shown in FIG. 1 using standard cloning procedures. The coding sequence (CDS) of PBw is shown under SEQ ID NO: 17, the coding sequence (CDS) of haPB1 is shown under SEQ ID NO: 19 and the coding sequence (CDS) of haPB2 is shown under SEQ ID NO: 21.

The constructs were ligated into an expression vector, which allows transient expression of the transposase variants under control of the CMV promoter. General procedures for constructing expression plasmids are described in Sambrook, J E. F. Fritsch and T. Maniatis: Cloning I/II/III, A Laboratory Manual New York/Cold Spring Harbor Laboratory Press, 1989, Second Edition.

Example 2

Construction of the Transposon Plasmids

Figure 2A:
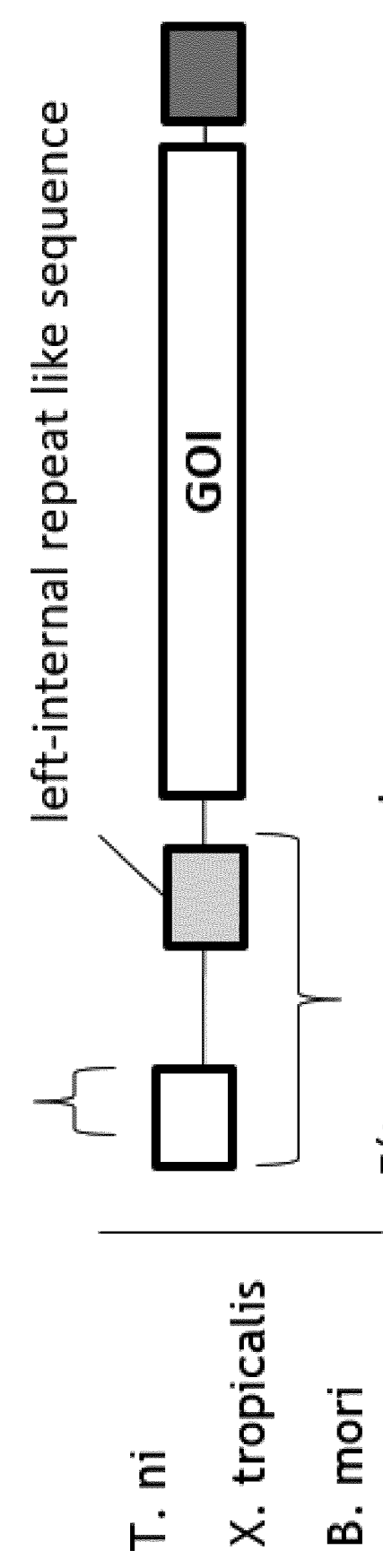
FIG. 2: Tested variants of transposon end sequences (TES). A: schematic representation of transposon B: Tested transposon variants

Transposons were created containing variants of natural and artificial PB transposon end sequences and tested for their ability to be recognized by the PB transposase. The tested constructs are shown in FIG. 2*b*. The nucleotide sequences of the transposon end sequences are listed here under SEQ ID NO: 13 (piggyBac, *Trichoplusia ni*, 5'-transposon end sequence (wt) (357 bp)), SEQ ID NO: 14 (piggyBac, *Trichoplusia ni*, 3'-transposon end sequence (wt)), SEQ ID NO: 6 (piggyBac, *Trichoplusia ni*, 5'-transposon end sequence (wt) (248 bp)), SEQ ID NO: 11 (piggyBac,

*Trichoplusia ni*, minimal 5'-transposon end sequence (wt)), SEQ ID NO: 12 (piggyBac, *Trichoplusia ni*, minimal 3'-transposon end sequence (wt)), SEQ ID NO: 16 (piggy-Bac, artificial 5'-transposon end sequence (357 bp)) and SEQ ID NO: 15 (piggyBac, artificial 5'-transposon end sequence (248 bp)). The transposon end sequences were integrated in the empty expression vectors PBGGPEx2.0m and PBGGPEx2.0p in 5' and 3' position to the bacterial backbone sequence with bacterial replication origin and antibiotic resistance gene.

Figure 3:
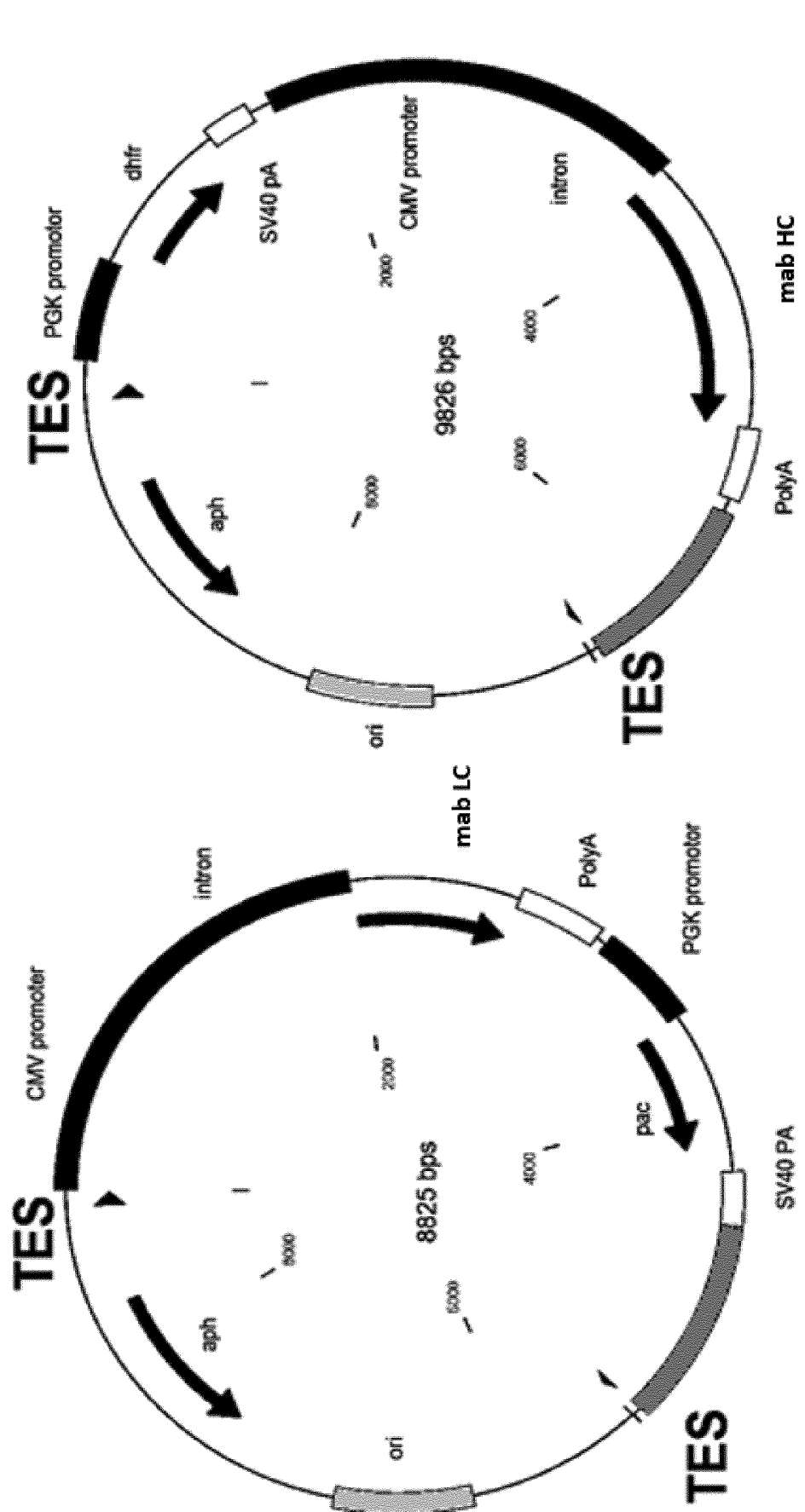
FIG. 3: Maps of transposon expression vectors. Promoter regions are shown as black blocks, Polyadenylation signals (PolyA) are shown as white boxes. Antibiotic resistance genes, selection marker genes and the coding region for the light chain gene or rather the heavy chain gene are shown as arrows: pac=puromycin-N-acetyltransferase; dhfr=dehydrofolate reductase; aph=kanamycin resistance. The location of the tested transposon end sequences (TES) are shown as triangles.

Synthetic heavy or rather light chain fragments of an monoclonal antibody assembled with a signal peptide were ligated into the transposon containing empty expression vectors to generate the plasmids shown in FIG. 3. General procedures for constructing expression plasmids are described in Sambrook, J E. F. Fritsch and T. Maniatis: Cloning I/II/III, A Laboratory Manual New York/Cold Spring Harbor Laboratory Press, 1989, Second Edition.

Example 3

Generation and Analysis of Clone Pools

As starter cell line the dihydrofolate reductase-deficient CHO cell line, CHO/DG44 [Urlaub et al., 1986, Proc Natl Acad Sci USA. 83 (2): 337-341] was used. The cell line was maintained in serum-free medium. Plasmids containing one of the transposon variants and transient expression vectors for expression of one of the transposase variants each were transfected by electroporation according to the manufacturer's instructions (Neon Transfection System, Thermo Fisher Scientific). In each transfection 1.5 µg of circular HC and LC transposon vector DNA and 1.2 µg of circular transposase DNA were used. Transfectants were subjected to selection with puromycin and methotrexate to eliminate untransfected cells, as well as non- and low-producer. Two consecutive series of transfections and selections were performed using the same vector combinations, DNA amounts and selection conditions. After a selection period of two weeks selection pressure was removed and resulting clone pools were subjected to Fed-batch processes under generic conditions with defined seeding cell densities. Fed batch processes were performed in shake flasks (SF125, Corning) with working volumes of 30 mL in chemically defined culture medium. A chemically defined feed was applied every two days following a generic feeding regiment. Viability were measured using a Vi-CELL viability analyzer (Beckman Coulter). Antibody concentrations of cell culture supernatant samples were determined by the Octet® RED96 System (Fortebio) against purified material of the expressed antibody as standard curve.

Figure 4A:
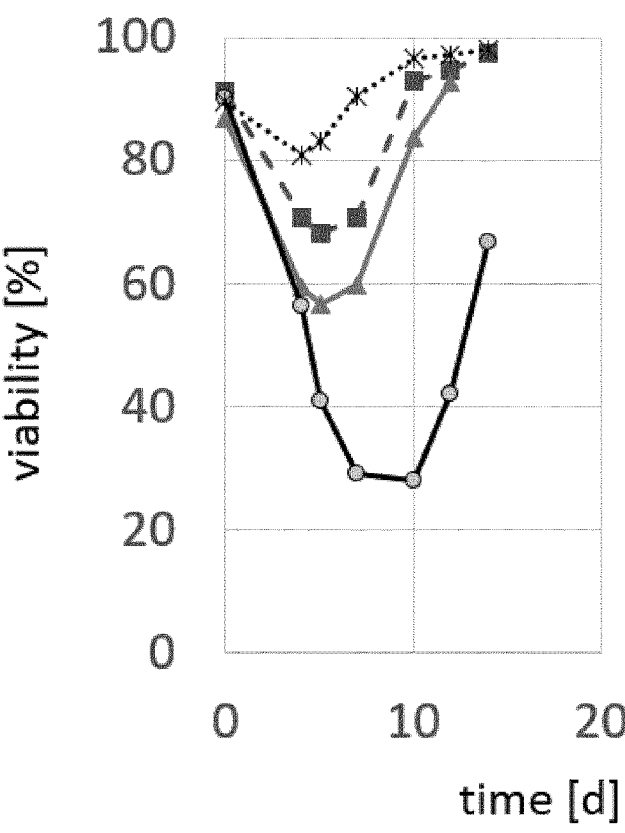
FIG. 4*a*: Viability recovery during selection phase. A: circles: PB minimal wild type TES Transposable Element and PBw; triangles: PB wild type TES Transposable Element (5'TES 247 bp) and PBw; squares: PB artificial TES Transposable Element (5'TES 247 bp) and PBw; asterisk: PB artificial TES (5'TES 247 bp) and haPB2 B: Viability at day 5 post selection start of PB wild type TES Transposable Element and PB artificial TES Transposable Element and PBw.
Figure 4B:
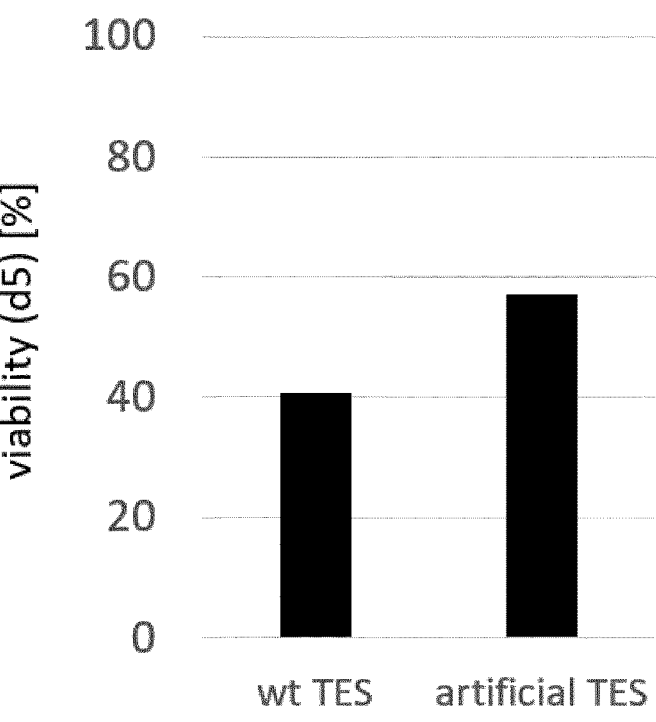

FIG. 4 shows viability recovery during selection phase of transfectants generated with wild type PB transposase or hyperactive transposase haPB2 and the transposons of Example 2. A faster recovery of viability was observed compared to the wild type transposons. The faster recovery of viability was observed by using hyperactive transposase in combination with a transposon comprising an artificial TES.

Figure 5:
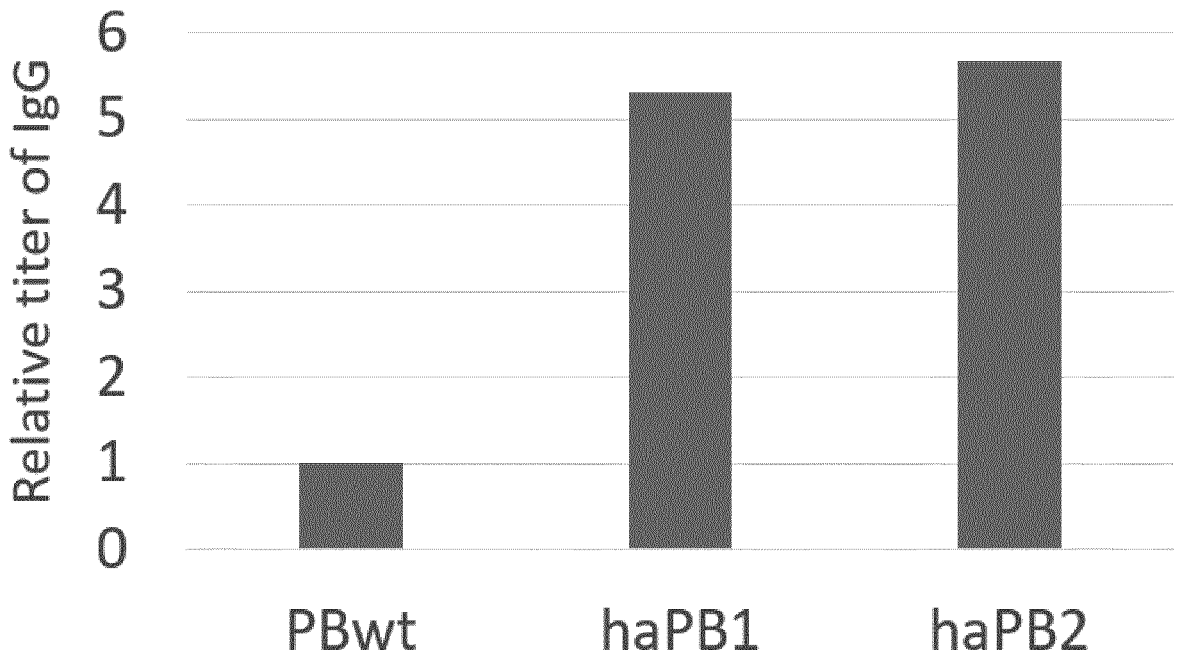
FIG. 5: Fed Batch IgG antibody titer concentrations of CHO-DG44 clones pools after brief selection. Relative day 14 titers derived from PBw and hyperactive transposase variants.

FIG. 5 shows the fed batch results at day 14 of clone pools derived from wt PB transposase and hyperactive transposase variants by using the PB minimal wild type TES Transposons. An increase in titer was observed compared to the wild type transposase for the hyperactive transposase variants (5 to 6 fold).

Sequence Listing Summary

SEQ ID NO: 1 piggyBac, *Trichoplusia ni*, left internal repeat wild-type (wt)

SEQ ID NO: 2 piggyBac-like, *Xenopus tropicalis*, left internal repeat (wt)

SEQ ID NO: 3 piggyBac-like, *Bombyx mori*, left internal repeat (wt)

SEQ ID NO: 4 piggyBac-like, *Mytois lucifugus* #1, left internal repeat (wt)

SEQ ID NO: 5 piggyBac-like, *Mytois lucifugus* #2, left internal repeat (wt)

SEQ ID NO: 6 piggyBac, *Trichoplusia ni,* 5'-transposon end sequence (wt), encompassing SEQ ID NO: 1 (wt) (248 bp)

SEQ ID NO: 7 piggyBac-like, *Xenopus tropicalis,* 5'-transposon end sequence (wt), encompassing SEQ ID NO: 2 (wt)

SEQ ID NO: 8 piggyBac-like, *Bombyx mori,* 5'-transposon end sequence (wt), encompassing SEQ ID NO: 3 (wt)

SEQ ID NO: 9 piggyBac-like, *Mytois lucifugus* #1, 5'-transposon end sequence (wt), encompassing SEQ ID NO: 4 (wt)

SEQ ID NO: 10 piggyBac-like, *Mytois lucifugus* #2, 5'-transposon end sequence (wt), encompassing SEQ ID NO: 5 (wt)

SEQ ID NO: 11 piggyBac, *Trichoplusia ni*, minimal 5'-transposon end sequence (wt)

SEQ ID NO: 12 piggyBac, *Trichoplusia ni*, minimal 3'-transposon end sequence (wt)

SEQ ID NO: 13 piggyBac, *Trichoplusia ni,* 5'-transposon end sequence (wt) (357 bp)

SEQ ID NO: 14 piggyBac, *Trichoplusia ni,* 3'-transposon end sequence (wt)

SEQ ID NO: 15 piggyBac, artificial 5'-transposon end sequence (248 bp)

SEQ ID NO: 16 piggyBac, artificial 5'-transposon end sequence (357 bp)

SEQ ID NO: 17 wt piggyBac transposase, *Trichoplusia ni*, DNA

SEQ ID NO: 18 wt piggyBac transposase, *Trichoplusia ni*, protein

SEQ ID NO: 19 piggyBac transposase mutant haPB1, DNA

SEQ ID NO: 20 piggyBac transposase mutant haPB1, protein

SEQ ID NO: 21 piggyBac transposase mutant haPB2, DNA

SEQ ID NO: 22 piggyBac transposase mutant haPB2, protein

SEQ ID NO: 23 piggyBac, *Trichoplusia ni*, left repeat sequence (wt)

SEQ ID NO: 24 piggyBac-like, *Xenopus tropicalis*, left repeat sequence (wt)

SEQ ID NO: 25 piggyBac-like, *Bombyx mori*, left repeat sequence (wt)

SEQ ID NO: 26 piggyBac-like, *Mytois lucifugus* #1, left repeat sequence (wt)

SEQ ID NO: 27 piggyBac-like, *Mytois lucifugus* #2, left repeat sequence (wt)

SEQ ID NO: 28: piggyBac, artificial left internal repeat

The invention claimed is:

1. A polypeptide comprising a piggyBac transposase, wherein the piggyBac transposase (i) has an amino acid sequence according to SEQ ID NO: 18, wherein isoleucine (I) at amino acid position 30 is replaced by alanine (A) (I30A), methionine (M) at amino acid position 282 is replaced by leucine (L) (M282L), and asparagine (N) at amino acid position 538 is replaced by arginine (R) (N538R), or is a variant thereof which is at least 90% identical to SEQ ID NO: 18, wherein isoleucine (I) at amino acid position 30 or at an amino acid position corresponding thereto is replaced by alanine (A) (I30A), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R); or (ii) has an amino acid sequence according to SEQ ID NO: 18, wherein isoleucine (I) at amino acid position 30 is replaced by alanine (A) (I30A), glutamine (Q) at amino acid position 118 is replaced by proline (P) (0118P), methionine (M) at amino acid position 185 is replaced by valine (V) (M185V), methionine (M) at amino acid position 282 is replaced by leucine (L) (M282L), and asparagine (N) at amino acid position 538 is replaced by arginine (R) (N538R), or is a variant thereof which is at least 90% identical to SEQ ID NO: 18, wherein isoleucine (I) at amino acid position 30 or at an amino acid position corresponding thereto is replaced by alanine (A) (I30A), glutamine (Q) at amino acid position 118 or at an amino acid position corresponding thereto is replaced by proline (P) (Q118P), methionine (M) at amino acid position 185 or at an amino acid position corresponding thereto is replaced by valine (V) (M185V), methionine (M) at amino acid position 282 or at an amino acid position corresponding thereto is replaced by leucine (L) (M282L), and asparagine (N) at amino acid position 538 or at an amino acid position corresponding thereto is replaced by arginine (R) (N538R); or (iii) has an amino acid sequence according to SEQ ID NO: 22, or is a variant thereof which is at least 90% identical to SEQ ID NO: 22, wherein said variant comprises alanine (A) at amino acid position 30 or at an amino acid position corresponding thereto, leucine (L) at amino acid position 282 or at an amino acid position corresponding thereto and arginine (R) at amino acid position 538 or at an amino acid position corresponding thereto; or (iv) has an amino acid sequence according to SEQ ID NO: 20, or is a variant thereof which is at least 90% identical to SEQ ID NO: 20, wherein said variant comprises alanine (A) at amino acid position 30 or at an amino acid position corresponding thereto, proline (P) at amino acid position 118 or at an amino acid position corresponding thereto, amino acid valine (V) at amino acid position 185 or at an amino acid position corresponding thereto, leucine (L) at amino acid position 282 or at an amino acid position corresponding thereto and arginine (R) at amino acid position 538 or at an amino acid position corresponding thereto.

2. The polypeptide of claim 1, wherein the polypeptide comprises at least one heterologous chromatin reader domain (CRD).

3. The polypeptide of claim 1, wherein at least one heterologous CRD is connected to the transposase via a linker.

4. The polypeptide of claim 3, wherein the CRD recognises histone methylation degree and/or acetylation state of histones.

5. A polynucleotide encoding the polypeptide of claim 1.

6. A vector comprising the polynucleotide of claim 5.

7. A method for producing a transgenic cell comprising the steps of:

(i) providing a cell, and (ii) introducing a transposable element comprising piggyBac or piggyBac-like terminal repeats (TRs) flanking a gene, and a polypeptide of claim 1 or a polynucleotide encoding the polypeptide into the cell, thereby producing the transgenic cell comprising the gene integrated in its genome.

8. The method of claim 7, wherein the transposable element of comprises at least one polynucleotide of interest.

9. The method of claim 8, wherein the at least one polynucleotide of interest is flanked by terminal repeats (TRs).

10. A kit comprising a polynucleotide comprising a transposable element comprising piggyBac or piggyBac-like terminal repeats (TRs), and a polypeptide of claim 1 or a second polynucleotide encoding the polypeptide, and a container.

11. The kit of claim 10, wherein the transposable element comprises at least one polynucleotide of interest, or at least one cloning site for inserting at least one polynucleotide of interest.

\* \* \* \* \*

SEQUENCE LISTING

<160> NUMBER OF SEQ ID NOS: 28

<210> SEQ ID NO 1
<211> LENGTH: 17
<212> TYPE: DNA
<213> ORGANISM: Trichoplusia ni

<400> SEQUENCE: 1
tgagtcaaaa tgacgca                                               17

<210> SEQ ID NO 2
<211> LENGTH: 13
<212> TYPE: DNA
<213> ORGANISM: Xenopus tropicalis

<400> SEQUENCE: 2
tggcagtaaa agg                                                   13

<210> SEQ ID NO 3
<211> LENGTH: 17
<212> TYPE: DNA
<213> ORGANISM: Bombyx mori

<400> SEQUENCE: 3
gggtatgtta taccctg                                               17

<210> SEQ ID NO 4
<211> LENGTH: 16
<212> TYPE: DNA
<213> ORGANISM: Myotis lucifugus

<400> SEQUENCE: 4
gagccgtctt aactcg                                                16

<210> SEQ ID NO 5
<211> LENGTH: 16
<212> TYPE: DNA
<213> ORGANISM: Myotis lucifugus

<400> SEQUENCE: 5
cgagtgttct cgtttt                                                16

<210> SEQ ID NO 6
<211> LENGTH: 248
<212> TYPE: DNA
<213> ORGANISM: Trichoplusia ni

<400> SEQUENCE: 6
ccctagaaag atagtctgcg taaaattgac gcatggctag ctgaaatatt gctctctctt      60
tctaaatagc gcgaatccgt cgctgtgcat ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgacttta agatttaact catacgataa      240
ttgctagc                                                            248

<210> SEQ ID NO 7
<211> LENGTH: 97
<212> TYPE: DNA
<213> ORGANISM: Xenopus tropicalis

<400> SEQUENCE: 7
cccttgatgt caataccaaa ccaaaagcag cgctaaggtt gatccttaac cttttttactg     60 ccaatgacgc atgggatacg tcgtggcagt aaaaggg                              97

<210> SEQ ID NO 8
<211> LENGTH: 204
<212> TYPE: DNA
<213> ORGANISM: Bombyx mori

<400> SEQUENCE: 8
cccggcgagc atgaggcagg gtatctcata ccctggtaaa attttaaagt tgtgtatttt      60
ataaaatttt cgtctgacaa cactagcgcg ctcagtagct ggaggcagga gcgtgcggga     120
ggggatagtg gcgtgatcgc agtgtggcac gggacaccgg cgagatattc gtgtgcaaac     180
ctgtttcggg tatgttatac cctg                                            204

<210> SEQ ID NO 9
<211> LENGTH: 74
<212> TYPE: DNA
<213> ORGANISM: Myotis lucifugus

<400> SEQUENCE: 9
cacttggatt gcgggaaacg agttaagtcg gctcgcgtga attgcgcgta ctccgcggga      60
gccgtcttaa ctcg                                                       74

<210> SEQ ID NO 10
<211> LENGTH: 78
<212> TYPE: DNA
<213> ORGANISM: Myotis lucifugus

<400> SEQUENCE: 10
cacattgcgt accgctcacg agttttctcg tgtttcgcgc gccatctgtt aaggaccgct      60
cacgagtgtt ctcgtttt                                                   78

<210> SEQ ID NO 11
<211> LENGTH: 35
<212> TYPE: DNA
<213> ORGANISM: Trichoplusia ni

<400> SEQUENCE: 11
ccctagaaag atagtctgcg taaaattgac gcatg                                35

<210> SEQ ID NO 12
<211> LENGTH: 67
<212> TYPE: DNA
<213> ORGANISM: Trichoplusia ni

<400> SEQUENCE: 12
ttaacatgcg tcaattttac gcatgattat ctttaacgta cgtcacaata tgattatctt      60
tctaggg                                                               67

<210> SEQ ID NO 13
<211> LENGTH: 357
<212> TYPE: DNA
<213> ORGANISM: Trichoplusia ni

<400> SEQUENCE: 13
ccctagaaag atagtctgcg taaaattgac gcatggctag ctgaaatatt gctctctctt      60
tctaaatagc gcgaatccgt cgctgtgcat ttaggacatc tcagtcgccg cttggagctc     120
ccgtgaggcg tgcttgtcaa tgcggtaagt gtcactgatt ttgaactata acgaccgcgt     180

-continued

```
gagtcaaaat gacgcatgat tatctttac gtgactttta agatttaact catacgataa       240
ttatattgtt atttcatgtt ctacttacgt gataacttat tatatatata ttttcttgtt       300
atagatatcg tgactaatat ataataaact ttgatgagaa tcaatctttt ctttcag         357

<210> SEQ ID NO 14
<211> LENGTH: 354
<212> TYPE: DNA
<213> ORGANISM: Trichoplusia ni

<400> SEQUENCE: 14
ttttctcctt acgcatctgt gcggtatttc acaccgcatg ggcagaatac aatggaaagt        60
ccctattgac tcaggcctgt ttaaaagttt tgttacttta tagaagaaat tttgagtttt       120
tgtttttttt taataaataa ataaacataa ataaattgtt tgttgaattt attattagta       180
tgtaagtgta aatataataa aacttaatat ctattcaaat taataaataa acctcgatat       240
acagaccgat aaaacacggt ggccacgcgt tgggcctcgg tggccacgcg tcatgcgtca       300
attttacgca tgattatctt taacgtacgt cacaatatga ttatctttct aggg           354

<210> SEQ ID NO 15
<211> LENGTH: 248
<212> TYPE: DNA
<213> ORGANISM: Artificial Sequence
<220> FEATURE:
<223> OTHER INFORMATION: Transposon end

<400> SEQUENCE: 15
ccctagaaag atagtctgcg taaaattgac gcatggctag ctgaaatatt gctctctctt        60
tctaaatagc gcgaatccgt cgctgtgcat ttaggacatc tcagtcgccg cttggagctc       120
ccgtgaggcg tgcttgtcaa tgcggtaagt gtcactgatt ttgaactata acgaccgcgt       180
gcgtcaattt tacgcatgat tatctttac gtgactttta agatttaact catacgataa       240
ttgctagc                                                              248

<210> SEQ ID NO 16
<211> LENGTH: 357
<212> TYPE: DNA
<213> ORGANISM: Artificial Sequence
<220> FEATURE:
<223> OTHER INFORMATION: Transposon end

<400> SEQUENCE: 16
ccctagaaag atagtctgcg taaaattgac gcatggctag ctgaaatatt gctctctctt        60
tctaaatagc gcgaatccgt cgctgtgcat ttaggacatc tcagtcgccg cttggagctc       120
ccgtgaggcg tgcttgtcaa tgcggtaagt gtcactgatt ttgaactata acgaccgcgt       180
gcgtcaattt tacgcatgat tatctttac gtgactttta agatttaact catacgataa       240
ttatattgtt atttcatgtt ctacttacgt gataacttat tatatatata ttttcttgtt       300
atagatatcg tgactaatat ataataaact ttgatgagaa tcaatctttt ctttcag         357

<210> SEQ ID NO 17
<211> LENGTH: 1785
<212> TYPE: DNA
<213> ORGANISM: Trichoplusia ni
<220> FEATURE:
<221> NAME/KEY: CDS
<222> LOCATION: (1)..(1782)

<400> SEQUENCE: 17
```

-continued

```
atg ggc tct agc ctg gac gac gag cac att ctg tct gcc ctg ctg cag        48
Met Gly Ser Ser Leu Asp Asp Glu His Ile Leu Ser Ala Leu Leu Gln
1               5                   10                  15 tcc gac gat gaa ctc gtg ggc gaa gat tcc gac tcc gag atc tct gac        96
Ser Asp Asp Glu Leu Val Gly Glu Asp Ser Asp Ser Glu Ile Ser Asp
            20                  25                  30 cac gtg tcc gag gac gac gtg cag tct gat acc gag gaa gcc ttc atc       144
His Val Ser Glu Asp Asp Val Gln Ser Asp Thr Glu Glu Ala Phe Ile
        35                  40                  45 gac gag gtg cac gaa gtg cag cct acc tct tcc ggc tct gag atc ctg       192
Asp Glu Val His Glu Val Gln Pro Thr Ser Ser Gly Ser Glu Ile Leu
    50                  55                  60 gac gag cag aac gtg atc gag cag cct gga tcc tct ctg gcc tcc aac       240
Asp Glu Gln Asn Val Ile Glu Gln Pro Gly Ser Ser Leu Ala Ser Asn
65                  70                  75                  80 aga atc ctg aca ctg ccc cag aga acc atc cgg ggc aag aac aag cac       288
Arg Ile Leu Thr Leu Pro Gln Arg Thr Ile Arg Gly Lys Asn Lys His
                85                  90                  95 tgc tgg tcc acc tcc aag tct acc cgg cgg tct aga gtg tcc gct ctg       336
Cys Trp Ser Thr Ser Lys Ser Thr Arg Arg Ser Arg Val Ser Ala Leu
            100                 105                 110 aat att gtg cgg tcc cag agg ggc ccc acc aga atg tgc cgg aac atc       384
Asn Ile Val Arg Ser Gln Arg Gly Pro Thr Arg Met Cys Arg Asn Ile
        115                 120                 125 tac gac cct ctg ctg tgt ttc aag ctg ttc ttc acc gac gag atc atc       432
Tyr Asp Pro Leu Leu Cys Phe Lys Leu Phe Phe Thr Asp Glu Ile Ile
    130                 135                 140 agc gag atc gtg aag tgg acc aac gcc gag atc agc ctg aag cgg cgg       480
Ser Glu Ile Val Lys Trp Thr Asn Ala Glu Ile Ser Leu Lys Arg Arg
145                 150                 155                 160 gaa tct atg acc ggc gcc acc ttc aga gac acc aac gag gat gag atc       528
Glu Ser Met Thr Gly Ala Thr Phe Arg Asp Thr Asn Glu Asp Glu Ile
                165                 170                 175 tac gcc ttc ttc ggc atc ctg gtc atg aca gcc gtg cgg aag gac aac       576
Tyr Ala Phe Phe Gly Ile Leu Val Met Thr Ala Val Arg Lys Asp Asn
            180                 185                 190 cac atg tcc acc gac gac ctg ttc gac aga tcc ctg tcc atg gtg tac       624
His Met Ser Thr Asp Asp Leu Phe Asp Arg Ser Leu Ser Met Val Tyr
        195                 200                 205 gtg tcc gtg atg agc cgg gac aga ttc gac ttc ctg atc cgg tgc ctg       672
Val Ser Val Met Ser Arg Asp Arg Phe Asp Phe Leu Ile Arg Cys Leu
    210                 215                 220 cgg atg gac gac aag tcc atc aga ccc aca ctg cgc gag aac gac gtg       720
Arg Met Asp Asp Lys Ser Ile Arg Pro Thr Leu Arg Glu Asn Asp Val
225                 230                 235                 240 ttc aca cct gtg cgg aag atc tgg gac ctg ttc atc cac cag tgc atc       768
Phe Thr Pro Val Arg Lys Ile Trp Asp Leu Phe Ile His Gln Cys Ile
                245                 250                 255 cag aac tac acc cct ggc gct cac ctg acc atc gat gaa cag ctg ctg       816
Gln Asn Tyr Thr Pro Gly Ala His Leu Thr Ile Asp Glu Gln Leu Leu
            260                 265                 270 ggc ttc aga ggc aga tgc ccc ttc aga atg tac atc ccc aac aag ccc       864
Gly Phe Arg Gly Arg Cys Pro Phe Arg Met Tyr Ile Pro Asn Lys Pro
        275                 280                 285 tct aag tac ggc atc aag atc ctg atg atg tgc gac tcc ggc acc aag       912
Ser Lys Tyr Gly Ile Lys Ile Leu Met Met Cys Asp Ser Gly Thr Lys
    290                 295                 300 tac atg atc aac ggc atg ccc tac ctc ggc aga ggc acc caa aca aat       960
Tyr Met Ile Asn Gly Met Pro Tyr Leu Gly Arg Gly Thr Gln Thr Asn
305                 310                 315                 320
```

-continued

```
ggc gtg cca ctg ggc gag tac tat gtg aaa gaa ctg tcc aag cct gtg     1008
Gly Val Pro Leu Gly Glu Tyr Tyr Val Lys Glu Leu Ser Lys Pro Val
            325                 330                 335 cac ggc tcc tgc aga aac atc acc tgt gac aac tgg ttc acc agc att     1056
His Gly Ser Cys Arg Asn Ile Thr Cys Asp Asn Trp Phe Thr Ser Ile
            340                 345                 350 cct ctg gcc aag aac ctg ctg caa gag ccc tac aag ctg aca atc gtg     1104
Pro Leu Ala Lys Asn Leu Leu Gln Glu Pro Tyr Lys Leu Thr Ile Val
            355                 360                 365 ggc acc gtg cgg tcc aac aag cgg gaa att cct gag gtg ctg aag aac     1152
Gly Thr Val Arg Ser Asn Lys Arg Glu Ile Pro Glu Val Leu Lys Asn
            370                 375                 380 tct cgg tcc aga cct gtg ggc acc tcc atg ttc tgt ttc gac ggc cct     1200
Ser Arg Ser Arg Pro Val Gly Thr Ser Met Phe Cys Phe Asp Gly Pro
385                 390                 395                 400 ctg aca ctg gtg tcc tac aag cct aag cct gcc aag atg gtg tac ctg     1248
Leu Thr Leu Val Ser Tyr Lys Pro Lys Pro Ala Lys Met Val Tyr Leu
                405                 410                 415 ctg tcc tcc tgt gac gag gac gcc agc atc aat gag tcc acc ggc aag     1296
Leu Ser Ser Cys Asp Glu Asp Ala Ser Ile Asn Glu Ser Thr Gly Lys
            420                 425                 430 ccc cag atg gtc atg tac tac aac cag acc aaa ggc ggc gtg gac acc     1344
Pro Gln Met Val Met Tyr Tyr Asn Gln Thr Lys Gly Gly Val Asp Thr
            435                 440                 445 ctg gac cag atg tgc tct gtg atg acc tgc tcc aga aag acc aac aga     1392
Leu Asp Gln Met Cys Ser Val Met Thr Cys Ser Arg Lys Thr Asn Arg
            450                 455                 460 tgg ccc atg gct ctg ctg tac ggc atg atc aat atc gcc tgc atc aac     1440
Trp Pro Met Ala Leu Leu Tyr Gly Met Ile Asn Ile Ala Cys Ile Asn
465                 470                 475                 480 agc ttc atc atc tac tcc cac aac gtg tcc tcc aag ggc gag aag gtg     1488
Ser Phe Ile Ile Tyr Ser His Asn Val Ser Ser Lys Gly Glu Lys Val
                485                 490                 495 cag tcc cgg aag aaa ttc atg cgg aac ctg tat atg tcc ctg acc tcc     1536
Gln Ser Arg Lys Lys Phe Met Arg Asn Leu Tyr Met Ser Leu Thr Ser
            500                 505                 510 agc ttc atg aga aag cgg ctg gaa gcc cct act ctg aag aga tac ctg     1584
Ser Phe Met Arg Lys Arg Leu Glu Ala Pro Thr Leu Lys Arg Tyr Leu
            515                 520                 525 cgg gac aac atc tcc aac atc ctg cct aac gag gtg ccc ggc acc agc     1632
Arg Asp Asn Ile Ser Asn Ile Leu Pro Asn Glu Val Pro Gly Thr Ser
            530                 535                 540 gac gat tct aca gag gaa cct gtg atg aag aag cgg acc tac tgc acc     1680
Asp Asp Ser Thr Glu Glu Pro Val Met Lys Lys Arg Thr Tyr Cys Thr
545                 550                 555                 560 tac tgt ccc tcc aag atc cgg cgg aag gcc aac gcc tct tgc aaa aag     1728
Tyr Cys Pro Ser Lys Ile Arg Arg Lys Ala Asn Ala Ser Cys Lys Lys
                565                 570                 575 tgc aag aaa gtg atc tgc cgc gag cac aac atc gac atg tgc cag tct     1776
Cys Lys Lys Val Ile Cys Arg Glu His Asn Ile Asp Met Cys Gln Ser
            580                 585                 590 tgt ttc tga                                                         1785
Cys Phe <210> SEQ ID NO 18
<211> LENGTH: 594
<212> TYPE: PRT
<213> ORGANISM: Trichoplusia ni

<400> SEQUENCE: 18
```

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415
```

```
Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 19
<211> LENGTH: 1785
<212> TYPE: DNA
<213> ORGANISM: Artificial Sequence
<220> FEATURE:
<223> OTHER INFORMATION: Hyperactive Transposase
<220> FEATURE:
<221> NAME/KEY: CDS
<222> LOCATION: (1)..(1782)

<400> SEQUENCE: 19 atg ggc agc tct ctg gac gac gag cac atc ctg tct gcc ctg ctg cag       48
Met Gly Ser Ser Leu Asp Asp Glu His Ile Leu Ser Ala Leu Leu Gln
1               5                   10                  15 tct gac gat gaa ctc gtg ggc gaa gat tcc gac tcc gag gcc tct gac       96
Ser Asp Asp Glu Leu Val Gly Glu Asp Ser Asp Ser Glu Ala Ser Asp
                20                  25                  30 cat gtg tct gag gac gac gtg cag tcc gat acc gag gaa gcc ttc atc      144
His Val Ser Glu Asp Asp Val Gln Ser Asp Thr Glu Glu Ala Phe Ile
            35                  40                  45 gac gag gtg cac gaa gtg cag cct acc tct tcc ggc tct gag atc ctg      192
Asp Glu Val His Glu Val Gln Pro Thr Ser Ser Gly Ser Glu Ile Leu
        50                  55                  60 gac gag cag aac gtg atc gag cag cct gga tcc tct ctg gcc tcc aac      240
Asp Glu Gln Asn Val Ile Glu Gln Pro Gly Ser Ser Leu Ala Ser Asn
65                  70                  75                  80 aga atc ctg aca ctg ccc cag aga acc atc cgg ggc aag aac aag cac      288
Arg Ile Leu Thr Leu Pro Gln Arg Thr Ile Arg Gly Lys Asn Lys His
                85                  90                  95 tgc tgg tcc acc tcc aag tct acc cgg cgg tct aga gtg tcc gct ctg      336
Cys Trp Ser Thr Ser Lys Ser Thr Arg Arg Ser Arg Val Ser Ala Leu
            100                 105                 110 aat att gtg cgg tcc ccg agg ggc ccc acc aga atg tgc cgg aac atc      384
Asn Ile Val Arg Ser Pro Arg Gly Pro Thr Arg Met Cys Arg Asn Ile
            115                 120                 125
```

-continued

```
tac gac cct ctg ctg tgc ttc aag ctg ttc ttc acc gac gag atc atc        432
Tyr Asp Pro Leu Leu Cys Phe Lys Leu Phe Phe Thr Asp Glu Ile Ile
    130             135             140 tcc gag atc gtg aag tgg acc aac gcc gag atc tct ctg aag cgg cgc        480
Ser Glu Ile Val Lys Trp Thr Asn Ala Glu Ile Ser Leu Lys Arg Arg
145             150             155             160 gag tct atg acc ggc gcc acc ttc aga gac acc aac gag gat gag atc        528
Glu Ser Met Thr Gly Ala Thr Phe Arg Asp Thr Asn Glu Asp Glu Ile
                165             170             175 tac gcc ttc ttc ggc atc ctg gtc gtc aca gcc gtg cgg aag gac aac        576
Tyr Ala Phe Phe Gly Ile Leu Val Val Thr Ala Val Arg Lys Asp Asn
            180             185             190 cac atg tcc acc gac gac ctg ttc gac aga tcc ctg tcc atg gtg tac        624
His Met Ser Thr Asp Asp Leu Phe Asp Arg Ser Leu Ser Met Val Tyr
            195             200             205 gtg tcc gtg atg agc cgg gac aga ttc gac ttc ctg atc cgg tgc ctg        672
Val Ser Val Met Ser Arg Asp Arg Phe Asp Phe Leu Ile Arg Cys Leu
    210             215             220 cgg atg gac gac aag tcc atc aga ccc aca ctg cgc gag aac gac gtg        720
Arg Met Asp Asp Lys Ser Ile Arg Pro Thr Leu Arg Glu Asn Asp Val
225             230             235             240 ttc aca cct gtg cgg aag atc tgg gac ctg ttc atc cac cag tgc atc        768
Phe Thr Pro Val Arg Lys Ile Trp Asp Leu Phe Ile His Gln Cys Ile
                245             250             255 cag aac tac acc cct ggc gct cac ctg acc atc gac gaa cag ctg ctg        816
Gln Asn Tyr Thr Pro Gly Ala His Leu Thr Ile Asp Glu Gln Leu Leu
            260             265             270 ggc ttc aga ggc aga tgc cct ttc cgg ctg tac atc ccc aac aag ccc        864
Gly Phe Arg Gly Arg Cys Pro Phe Arg Leu Tyr Ile Pro Asn Lys Pro
    275             280             285 tct aag tac ggc atc aag atc ctg atg atg tgc gac tcc ggc acc aag        912
Ser Lys Tyr Gly Ile Lys Ile Leu Met Met Cys Asp Ser Gly Thr Lys
    290             295             300 tac atg atc aac ggc atg ccc tac ctc ggc aga ggc acc caa aca aat        960
Tyr Met Ile Asn Gly Met Pro Tyr Leu Gly Arg Gly Thr Gln Thr Asn
305             310             315             320 ggc gtg cca ctg ggc gag tac tac gtg aaa gaa ctg tcc aag cct gtg       1008
Gly Val Pro Leu Gly Glu Tyr Tyr Val Lys Glu Leu Ser Lys Pro Val
                325             330             335 cac ggc tcc tgc aga aac atc acc tgt gac aac tgg ttc acc agc att       1056
His Gly Ser Cys Arg Asn Ile Thr Cys Asp Asn Trp Phe Thr Ser Ile
            340             345             350 cct ctg gcc aag aac ctg ctg caa gag ccc tac aag ctg aca atc gtg       1104
Pro Leu Ala Lys Asn Leu Leu Gln Glu Pro Tyr Lys Leu Thr Ile Val
            355             360             365 ggc acc gtg cgg tcc aac aag cgg gaa att cct gag gtg ctg aag aac       1152
Gly Thr Val Arg Ser Asn Lys Arg Glu Ile Pro Glu Val Leu Lys Asn
    370             375             380 tct cgg tcc aga cct gtg ggc acc tcc atg ttc tgt ttc gac ggc cct       1200
Ser Arg Ser Arg Pro Val Gly Thr Ser Met Phe Cys Phe Asp Gly Pro
385             390             395             400 ctg aca ctg gtg tcc tac aag cct aag cct gcc aag atg gtg tac ctg       1248
Leu Thr Leu Val Ser Tyr Lys Pro Lys Pro Ala Lys Met Val Tyr Leu
            405             410             415 ctg tcc tcc tgt gac gag gac gcc agc atc aat gag tcc acc ggc aag       1296
Leu Ser Ser Cys Asp Glu Asp Ala Ser Ile Asn Glu Ser Thr Gly Lys
            420             425             430 ccc cag atg gtc atg tac tac aac cag acc aaa ggc ggc gtg gac acc       1344
Pro Gln Met Val Met Tyr Tyr Asn Gln Thr Lys Gly Gly Val Asp Thr
```

-continued

```
            435                 440                 445 ctg gac cag atg tgc tct gtg atg acc tgc tcc aga aag acc aac cgg      1392
Leu Asp Gln Met Cys Ser Val Met Thr Cys Ser Arg Lys Thr Asn Arg
    450                 455                 460 tgg cct atg gct ctg ctg tac ggc atg atc aat atc gcc tgc atc aac      1440
Trp Pro Met Ala Leu Leu Tyr Gly Met Ile Asn Ile Ala Cys Ile Asn
465                 470                 475                 480 agc ttc atc atc tac tcc cac aac gtg tcc tcc aag ggc gag aag gtg      1488
Ser Phe Ile Ile Tyr Ser His Asn Val Ser Ser Lys Gly Glu Lys Val
                485                 490                 495 cag tcc cgg aag aaa ttc atg cgg aac ctg tat atg tcc ctg acc tcc      1536
Gln Ser Arg Lys Lys Phe Met Arg Asn Leu Tyr Met Ser Leu Thr Ser
            500                 505                 510 agc ttc atg aga aag cgg ctg gaa gcc cct aca ctg aag aga tac ctg      1584
Ser Phe Met Arg Lys Arg Leu Glu Ala Pro Thr Leu Lys Arg Tyr Leu
            515                 520                 525 cgg gac aac atc tcc aac atc ctg cct aga gag gtg ccc ggc acc agc      1632
Arg Asp Asn Ile Ser Asn Ile Leu Pro Arg Glu Val Pro Gly Thr Ser
        530                 535                 540 gac gat tct aca gag gaa ccc gtg atg aag aag cgg acc tac tgc acc      1680
Asp Asp Ser Thr Glu Glu Pro Val Met Lys Lys Arg Thr Tyr Cys Thr
545                 550                 555                 560 tac tgt ccc tcc aag atc cgg cgg aag gcc aac gcc tct tgc aaa aag      1728
Tyr Cys Pro Ser Lys Ile Arg Arg Lys Ala Asn Ala Ser Cys Lys Lys
                565                 570                 575 tgc aag aaa gtg atc tgc cgc gag cac aac atc gac atg tgc cag tct      1776
Cys Lys Lys Val Ile Cys Arg Glu His Asn Ile Asp Met Cys Gln Ser
            580                 585                 590 tgt ttc tga                                                          1785
Cys Phe
```

<210> SEQ ID NO 20
<211> LENGTH: 594
<212> TYPE: PRT
<213> ORGANISM: Artificial Sequence
<220> FEATURE:
<223> OTHER INFORMATION: Synthetic Construct

<400> SEQUENCE: 20

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ala Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Pro Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
```

-continued

```
145                    150                    155                    160

Glu Ser Met Thr Gly Ala Thr Phe Arg Asp Thr Asn Glu Asp Glu Ile
                 165                    170                    175

Tyr Ala Phe Phe Gly Ile Leu Val Val Thr Ala Val Arg Lys Asp Asn
                 180                    185                    190

His Met Ser Thr Asp Asp Leu Phe Asp Arg Ser Leu Ser Met Val Tyr
                 195                    200                    205

Val Ser Val Met Ser Arg Asp Arg Phe Asp Phe Leu Ile Arg Cys Leu
                 210                    215                    220

Arg Met Asp Asp Lys Ser Ile Arg Pro Thr Leu Arg Glu Asn Asp Val
225                    230                    235                    240

Phe Thr Pro Val Arg Lys Ile Trp Asp Leu Phe Ile His Gln Cys Ile
                 245                    250                    255

Gln Asn Tyr Thr Pro Gly Ala His Leu Thr Ile Asp Glu Gln Leu Leu
                 260                    265                    270

Gly Phe Arg Gly Arg Cys Pro Phe Arg Leu Tyr Ile Pro Asn Lys Pro
                 275                    280                    285

Ser Lys Tyr Gly Ile Lys Ile Leu Met Met Cys Asp Ser Gly Thr Lys
                 290                    295                    300

Tyr Met Ile Asn Gly Met Pro Tyr Leu Gly Arg Gly Thr Gln Thr Asn
305                    310                    315                    320

Gly Val Pro Leu Gly Glu Tyr Tyr Val Lys Glu Leu Ser Lys Pro Val
                 325                    330                    335

His Gly Ser Cys Arg Asn Ile Thr Cys Asp Asn Trp Phe Thr Ser Ile
                 340                    345                    350

Pro Leu Ala Lys Asn Leu Leu Gln Glu Pro Tyr Lys Leu Thr Ile Val
                 355                    360                    365

Gly Thr Val Arg Ser Asn Lys Arg Glu Ile Pro Glu Val Leu Lys Asn
                 370                    375                    380

Ser Arg Ser Arg Pro Val Gly Thr Ser Met Phe Cys Phe Asp Gly Pro
385                    390                    395                    400

Leu Thr Leu Val Ser Tyr Lys Pro Lys Pro Ala Lys Met Val Tyr Leu
                 405                    410                    415

Leu Ser Ser Cys Asp Glu Asp Ala Ser Ile Asn Glu Ser Thr Gly Lys
                 420                    425                    430

Pro Gln Met Val Met Tyr Tyr Asn Gln Thr Lys Gly Gly Val Asp Thr
                 435                    440                    445

Leu Asp Gln Met Cys Ser Val Met Thr Cys Ser Arg Lys Thr Asn Arg
                 450                    455                    460

Trp Pro Met Ala Leu Leu Tyr Gly Met Ile Asn Ile Ala Cys Ile Asn
465                    470                    475                    480

Ser Phe Ile Ile Tyr Ser His Asn Val Ser Ser Lys Gly Glu Lys Val
                 485                    490                    495

Gln Ser Arg Lys Lys Phe Met Arg Asn Leu Tyr Met Ser Leu Thr Ser
                 500                    505                    510

Ser Phe Met Arg Lys Arg Leu Glu Ala Pro Thr Leu Lys Arg Tyr Leu
                 515                    520                    525

Arg Asp Asn Ile Ser Asn Ile Leu Pro Arg Glu Val Pro Gly Thr Ser
                 530                    535                    540

Asp Asp Ser Thr Glu Glu Pro Val Met Lys Lys Arg Thr Tyr Cys Thr
545                    550                    555                    560

Tyr Cys Pro Ser Lys Ile Arg Arg Lys Ala Asn Ala Ser Cys Lys Lys
                 565                    570                    575
```

-continued

```
Cys Lys Lys Val Ile Cys Arg Glu His Asn Ile Asp Met Cys Gln Ser
            580                 585                 590

Cys Phe

<210> SEQ ID NO 21
<211> LENGTH: 1785
<212> TYPE: DNA
<213> ORGANISM: Artificial Sequence
<220> FEATURE:
<223> OTHER INFORMATION: hyperactive Transposase
<220> FEATURE:
<221> NAME/KEY: CDS
<222> LOCATION: (1)..(1782)

<400> SEQUENCE: 21 atg ggc agc tct ctg gac gac gag cac atc ctg tct gcc ctg ctg cag        48
Met Gly Ser Ser Leu Asp Asp Glu His Ile Leu Ser Ala Leu Leu Gln
1               5                   10                  15 tct gac gat gaa ctc gtg ggc gaa gat tcc gac tcc gag gcc tct gac        96
Ser Asp Asp Glu Leu Val Gly Glu Asp Ser Asp Ser Glu Ala Ser Asp
            20                  25                  30 cat gtg tct gag gac gac gtg cag tcc gat acc gag gaa gcc ttc atc       144
His Val Ser Glu Asp Asp Val Gln Ser Asp Thr Glu Glu Ala Phe Ile
        35                  40                  45 gac gag gtg cac gaa gtg cag cct acc tct tcc ggc tct gag atc ctg       192
Asp Glu Val His Glu Val Gln Pro Thr Ser Ser Gly Ser Glu Ile Leu
    50                  55                  60 gac gag cag aac gtg atc gag cag cct gga tcc tct ctg gcc tcc aac       240
Asp Glu Gln Asn Val Ile Glu Gln Pro Gly Ser Ser Leu Ala Ser Asn
65                  70                  75                  80 aga atc ctg aca ctg ccc cag aga acc atc cgg ggc aag aac aag cac       288
Arg Ile Leu Thr Leu Pro Gln Arg Thr Ile Arg Gly Lys Asn Lys His
                85                  90                  95 tgc tgg tcc acc tcc aag tct acc cgg cgg tct aga gtg tcc gct ctg       336
Cys Trp Ser Thr Ser Lys Ser Thr Arg Arg Ser Arg Val Ser Ala Leu
            100                 105                 110 aat att gtg cgg tcc cag agg ggc ccc acc aga atg tgc cgg aac atc       384
Asn Ile Val Arg Ser Gln Arg Gly Pro Thr Arg Met Cys Arg Asn Ile
        115                 120                 125 tac gac cct ctg ctg tgc ttc aag ctg ttc ttc acc gac gag atc atc       432
Tyr Asp Pro Leu Leu Cys Phe Lys Leu Phe Phe Thr Asp Glu Ile Ile
    130                 135                 140 tcc gag atc gtg aag tgg acc aac gcc gag atc tct ctg aag cgg cgc       480
Ser Glu Ile Val Lys Trp Thr Asn Ala Glu Ile Ser Leu Lys Arg Arg
145                 150                 155                 160 gag tct atg acc ggc gcc acc ttc aga gac acc aac gag gat gag atc       528
Glu Ser Met Thr Gly Ala Thr Phe Arg Asp Thr Asn Glu Asp Glu Ile
                165                 170                 175 tac gcc ttc ttc ggc atc ctg gtc atg aca gcc gtg cgg aag gac aac       576
Tyr Ala Phe Phe Gly Ile Leu Val Met Thr Ala Val Arg Lys Asp Asn
            180                 185                 190 cac atg tcc acc gac gac ctg ttc gac aga tcc ctg tcc atg gtg tac       624
His Met Ser Thr Asp Asp Leu Phe Asp Arg Ser Leu Ser Met Val Tyr
        195                 200                 205 gtg tcc gtg atg agc cgg gac aga ttc gac ttc ctg atc cgg tgc ctg       672
Val Ser Val Met Ser Arg Asp Arg Phe Asp Phe Leu Ile Arg Cys Leu
    210                 215                 220 cgg atg gac gac aag tcc atc aga ccc aca ctg cgc gag aac gac gtg       720
Arg Met Asp Asp Lys Ser Ile Arg Pro Thr Leu Arg Glu Asn Asp Val
225                 230                 235                 240
```

-continued

```
ttc aca cct gtg cgg aag atc tgg gac ctg ttc atc cac cag tgc atc        768
Phe Thr Pro Val Arg Lys Ile Trp Asp Leu Phe Ile His Gln Cys Ile
            245             250             255 cag aac tac acc cct ggc gct cac ctg acc atc gac gaa cag ctg ctg        816
Gln Asn Tyr Thr Pro Gly Ala His Leu Thr Ile Asp Glu Gln Leu Leu
            260             265             270 ggc ttc aga ggc aga tgc cct ttc cgg ctg tac atc ccc aac aag ccc        864
Gly Phe Arg Gly Arg Cys Pro Phe Arg Leu Tyr Ile Pro Asn Lys Pro
        275             280             285 tct aag tac ggc atc aag atc ctg atg atg tgc gac tcc ggc acc aag        912
Ser Lys Tyr Gly Ile Lys Ile Leu Met Met Cys Asp Ser Gly Thr Lys
    290             295             300 tac atg atc aac ggc atg ccc tac ctc ggc aga ggc acc caa aca aat        960
Tyr Met Ile Asn Gly Met Pro Tyr Leu Gly Arg Gly Thr Gln Thr Asn
305             310             315             320 ggc gtg cca ctg ggc gag tac tac gtg aaa gaa ctg tcc aag cct gtg       1008
Gly Val Pro Leu Gly Glu Tyr Tyr Val Lys Glu Leu Ser Lys Pro Val
            325             330             335 cac ggc tcc tgc aga aac atc acc tgt gac aac tgg ttc acc agc att       1056
His Gly Ser Cys Arg Asn Ile Thr Cys Asp Asn Trp Phe Thr Ser Ile
        340             345             350 cct ctg gcc aag aac ctg ctg caa gag ccc tac aag ctg aca atc gtg       1104
Pro Leu Ala Lys Asn Leu Leu Gln Glu Pro Tyr Lys Leu Thr Ile Val
        355             360             365 ggc acc gtg cgg tcc aac aag cgg gaa att cct gag gtg ctg aag aac       1152
Gly Thr Val Arg Ser Asn Lys Arg Glu Ile Pro Glu Val Leu Lys Asn
    370             375             380 tct cgg tcc aga cct gtg ggc acc tcc atg ttc tgt ttc gac ggc cct       1200
Ser Arg Ser Arg Pro Val Gly Thr Ser Met Phe Cys Phe Asp Gly Pro
385             390             395             400 ctg aca ctg gtg tcc tac aag cct aag cct gcc aag atg gtg tac ctg       1248
Leu Thr Leu Val Ser Tyr Lys Pro Lys Pro Ala Lys Met Val Tyr Leu
            405             410             415 ctg tcc tcc tgt gac gag gac gcc agc atc aat gag tcc acc ggc aag       1296
Leu Ser Ser Cys Asp Glu Asp Ala Ser Ile Asn Glu Ser Thr Gly Lys
        420             425             430 ccc cag atg gtc atg tac tac aac cag acc aaa ggc ggc gtg gac acc       1344
Pro Gln Met Val Met Tyr Tyr Asn Gln Thr Lys Gly Gly Val Asp Thr
    435             440             445 ctg gac cag atg tgc tct gtg atg acc tgc tcc aga aag acc aac cgg       1392
Leu Asp Gln Met Cys Ser Val Met Thr Cys Ser Arg Lys Thr Asn Arg
    450             455             460 tgg cct atg gct ctg ctg tac ggc atg atc aat atc gcc tgc atc aac       1440
Trp Pro Met Ala Leu Leu Tyr Gly Met Ile Asn Ile Ala Cys Ile Asn
465             470             475             480 agc ttc atc atc tac tcc cac aac gtg tcc tcc aag ggc gag aag gtg       1488
Ser Phe Ile Ile Tyr Ser His Asn Val Ser Ser Lys Gly Glu Lys Val
            485             490             495 cag tcc cgg aag aaa ttc atg cgg aac ctg tat atg tcc ctg acc tcc       1536
Gln Ser Arg Lys Lys Phe Met Arg Asn Leu Tyr Met Ser Leu Thr Ser
        500             505             510 agc ttc atg aga aag cgg ctg gaa gcc cct aca ctg aag aga tac ctg       1584
Ser Phe Met Arg Lys Arg Leu Glu Ala Pro Thr Leu Lys Arg Tyr Leu
        515             520             525 cgg gac aac atc tcc aac atc ctg cct aga gag gtg ccc ggc acc agc       1632
Arg Asp Asn Ile Ser Asn Ile Leu Pro Arg Glu Val Pro Gly Thr Ser
    530             535             540 gac gat tct aca gag gaa ccc gtg atg aag aag cgg acc tac tgc acc       1680
Asp Asp Ser Thr Glu Glu Pro Val Met Lys Lys Arg Thr Tyr Cys Thr
545             550             555             560
```

-continued

```
tac tgt ccc tcc aag atc cgg cgg aag gcc aac gcc tct tgc aaa aag        1728
Tyr Cys Pro Ser Lys Ile Arg Arg Lys Ala Asn Ala Ser Cys Lys Lys
                565                 570                 575 tgc aag aaa gtg atc tgc cgc gag cac aac atc gac atg tgc cag tct        1776
Cys Lys Lys Val Ile Cys Arg Glu His Asn Ile Asp Met Cys Gln Ser
            580                 585                 590 tgt ttc tga                                                            1785
Cys Phe
```

<210> SEQ ID NO 22
<211> LENGTH: 594
<212> TYPE: PRT
<213> ORGANISM: Artificial Sequence
<220> FEATURE:
<223> OTHER INFORMATION: Synthetic Construct

<400> SEQUENCE: 22

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ala Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
            85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Leu Tyr Ile Pro Asn Lys Pro
            275                 280                 285

Ser Lys Tyr Gly Ile Lys Ile Leu Met Met Cys Asp Ser Gly Thr Lys
        290                 295                 300
```

-continued

```
Tyr Met Ile Asn Gly Met Pro Tyr Leu Gly Arg Gly Thr Gln Thr Asn
305             310             315             320

Gly Val Pro Leu Gly Glu Tyr Tyr Val Lys Glu Leu Ser Lys Pro Val
            325             330             335

His Gly Ser Cys Arg Asn Ile Thr Cys Asp Asn Trp Phe Thr Ser Ile
            340             345             350

Pro Leu Ala Lys Asn Leu Leu Gln Glu Pro Tyr Lys Leu Thr Ile Val
            355             360             365

Gly Thr Val Arg Ser Asn Lys Arg Glu Ile Pro Glu Val Leu Lys Asn
            370             375             380

Ser Arg Ser Arg Pro Val Gly Thr Ser Met Phe Cys Phe Asp Gly Pro
385             390             395             400

Leu Thr Leu Val Ser Tyr Lys Pro Lys Pro Ala Lys Met Val Tyr Leu
            405             410             415

Leu Ser Ser Cys Asp Glu Asp Ala Ser Ile Asn Glu Ser Thr Gly Lys
            420             425             430

Pro Gln Met Val Met Tyr Tyr Asn Gln Thr Lys Gly Gly Val Asp Thr
            435             440             445

Leu Asp Gln Met Cys Ser Val Met Thr Cys Ser Arg Lys Thr Asn Arg
            450             455             460

Trp Pro Met Ala Leu Leu Tyr Gly Met Ile Asn Ile Ala Cys Ile Asn
465             470             475             480

Ser Phe Ile Ile Tyr Ser His Asn Val Ser Ser Lys Gly Glu Lys Val
            485             490             495

Gln Ser Arg Lys Lys Phe Met Arg Asn Leu Tyr Met Ser Leu Thr Ser
            500             505             510

Ser Phe Met Arg Lys Arg Leu Glu Ala Pro Thr Leu Lys Arg Tyr Leu
            515             520             525

Arg Asp Asn Ile Ser Asn Ile Leu Pro Arg Glu Val Pro Gly Thr Ser
            530             535             540

Asp Asp Ser Thr Glu Glu Pro Val Met Lys Lys Arg Thr Tyr Cys Thr
545             550             555             560

Tyr Cys Pro Ser Lys Ile Arg Arg Lys Ala Asn Ala Ser Cys Lys Lys
            565             570             575

Cys Lys Lys Val Ile Cys Arg Glu His Asn Ile Asp Met Cys Gln Ser
            580             585             590

Cys Phe
```

```
<210> SEQ ID NO 23
<211> LENGTH: 17
<212> TYPE: DNA
<213> ORGANISM: Trichoplusia ni

<400> SEQUENCE: 23
tgcgtaaaat tgacgca                                                    17

<210> SEQ ID NO 24
<211> LENGTH: 13
<212> TYPE: DNA
<213> ORGANISM: Xenopus tropicalis

<400> SEQUENCE: 24 ccttttttact gcc                                                       13

<210> SEQ ID NO 25
<211> LENGTH: 17
```

-continued

```
<212> TYPE: DNA
<213> ORGANISM: Bombyx mori

<400> SEQUENCE: 25
gggtatctca taccctg                                                                17

<210> SEQ ID NO 26
<211> LENGTH: 16
<212> TYPE: DNA
<213> ORGANISM: Mytois lucifugus

<400> SEQUENCE: 26
cgagttaagt cggctc                                                                 16

<210> SEQ ID NO 27
<211> LENGTH: 16
<212> TYPE: DNA
<213> ORGANISM: Mytois lucifugus

<400> SEQUENCE: 27
cgagttttct cgtgtt                                                                 16

<210> SEQ ID NO 28
<211> LENGTH: 17
<212> TYPE: DNA
<213> ORGANISM: Artificial Sequence
<220> FEATURE:
<223> OTHER INFORMATION: piggyBac Transposon, Trichoplusia ni,
      artificial left internal repeat

<400> SEQUENCE: 28
tgcgtcaatt ttacgca                                                               17
```